US010865176B2

(12) United States Patent
Chen

(10) Patent No.: US 10,865,176 B2
(45) Date of Patent: Dec. 15, 2020

(54) SMALL MOLECULE MODULATORS OF MICRORNA-34A

(71) Applicant: The Chinese University of Hong Kong, Shatin (CN)

(72) Inventor: Yangchao Chen, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 14/109,301

(22) Filed: Dec. 17, 2013

(65) Prior Publication Data

US 2014/0179799 A1    Jun. 26, 2014

Related U.S. Application Data

(60) Provisional application No. 61/745,348, filed on Dec. 21, 2012.

(51) Int. Cl.
| | | |
|---|---|---|
| C07C 49/84 | (2006.01) | |
| A61K 31/12 | (2006.01) | |
| A61K 45/06 | (2006.01) | |

(52) U.S. Cl.
CPC .............. *C07C 49/84* (2013.01); *A61K 31/12* (2013.01); *A61K 45/06* (2013.01)

(58) Field of Classification Search
USPC ....................................................... 514/685
See application file for complete search history.

(56) References Cited

U.S. PATENT DOCUMENTS

| 3,326,766 A | * | 6/1967 | Norman et al. ............ 514/419 |
| 2006/0135445 A1 | | 6/2006 | Yamazaki et al. |
| 2009/0182058 A1 | * | 7/2009 | Boumendjel et al. ........ 514/685 |

FOREIGN PATENT DOCUMENTS

| CN | 1744887 A | 3/2006 |
| CN | 102267888 A | 12/2011 |

OTHER PUBLICATIONS

Ribatti (Angiogenesis and anti-angiogenesis in hepatocellular carcinoma, Tumour Review, Mar. 2006, pp. 437-444).*
Bader (miR-34—a microRNA replacement therapy is headed to the clinic, Review Article, Jul. 2012, vol. 3, article 120, 1-9).*
Pisani et al., "Estimates of the Worldwide Mortality From 25 Cancers in 1990", *Int. J. Cancer*, 1999, vol. 83, pp. 18-29.
Carthew, "Gene regulation by microRNAs", *Current Opinion in Genetics & Development*, 2006, vol. 16, pp. 203-208.
Lewis et al., "Conserved Seed Pairing, Often Flanked by Adenosines, Indicates that Thousands of Human Genes are MicroRNA Targets", *Cell*, 2005, vol. 120, pp. 15-20.
Friedman et al., "Most mammalian mRNAs are conserved targets of microRNAs", *Genome Research*, 2008, vol. 19, pp. 92-105.
Selbach et al., "Widespread changes in protein synthesis induced by microRNAs", *Nature*, 2008, vol. 455, pp. 58-63.
Ha, "MicroRNAs in Human Diseases: From Cancer to Cardiovascular Disease", *Immune Network*, 2011, vol. 11, No. 3, pp. 135-154.
Hwang et al., "MicroRNAs in cell proliferation, cell death, and tumorigenesis", *British Journal of Cancer*, 2006, vol. 94, pp. 776-780.
Janssen et al., "Treatment of HCV Infection by Targeting MicroRNA", *The New England Journal of Medicine*, 2013, vol. 368, No. 18, pp. 1685-1694.
He et al., "A microRNA component of the p53 tumour suppressor network", *Nature*, 2007, vol. 447, pp. 1130-1135.
Welch et al., "MicroRNA-34a functions as a potential tumor suppressor by inducing apoptosis in neuroblastoma cells", *Oncogene*, 2007, vol. 26, pp. 5017-5022.
Sun et al., "Downregulation of CCND1 and CDK6 by miR-34a induces cell cycle arrest", *FEBS Letters*, 2008, vol. 582, pp. 1564-1568.
Ji et. al., "Delta-tocotrienol suppresses Notch-1 pathway by upregulating miR-34a in nonsmall cell lung cancer cells", *Int. J. Cancer*, 2012, vol. 131, pp. 2668-1677.
Toyota et al., "Epigenetic Silencing of MicroRNA-34b/c and B-Cell Translocation Gene 4 Is Associated with CpG Island Methylation in Colorectal Cancer", *Cancer Res.*, 2008, vol. 68, pp. 4123-4132.
Hashimi et al., "MicroRNA profiling identifies miR-34a and miR-21 and their target genes JAG1 and WNT1 in the coordinate regulation of dendritic cell differentiation", *Blood*, 2009, vol. 114, No. 2, pp. 404-414.
Li et al., "MicroRNA-34a Inhibits Glioblastoma Growth by Targeting Multiple Oncognes", *Cancer Res.*, 2009, vol. 69, pp. 7569-7576.
Yamakuchi et al., "miR-34a repression of SIRT1 regulates apoptosis", *PNAS*, 2008, vol. 105, No. 36, pp. 13421-13426.
Li et al., "miR-34a inhibits migration and invasion by downregulation of c-Met expression in human hepatocellular carcinoma cells", *Cancer Letters*, 2009, vol. 275, pp. 44-53.
Gumireddy et al., "Small-Molecule Inhibitors of MicroRNA miR-21 Function", *Angew. Chem. Int. Ed.*, 2008, vol. 47, pp. 7482-7484.
Young et al., "Small Molecules Modifiers of MicroRNA miR-122 Function for the Treatment of Hepatitis C Virus Infection and Hepatocellular Carcinoma", *J. Am. Chem. Soc.*, 2010, vol. 132, pp. 7976-7981.
Bommer et al., "p53-Mediated Activation of miRNA34 Candidate Tumor-Suppressor Genes", *Current Biology*, 2007, vol. 17, pp. 1298-1307.
Chang et al., "Transactivation of miR-34a by p53 Broadly Influences Gene Expression and Promotes Apoptosis", *Molecular Cell*, 2007, vol. 26, pp. 745-752.

(Continued)

*Primary Examiner* — Kathrien A Cruz
(74) *Attorney, Agent, or Firm* — Kilpatrick Townsend & Stockton LLP

(57) ABSTRACT

The present invention provides methods for identifying compounds that act as miR-34a modulators. The present invention also provides miR-34a modulators and compositions containing the modulators. The present invention further provides methods for treating diseases by administration of miR-34a modulators.

12 Claims, 22 Drawing Sheets

Specification includes a Sequence Listing.

(56) References Cited

OTHER PUBLICATIONS

Tarasov et al., "Differential Regulation of microRNAs by p53 Revealed by Massively Parallel Sequencing: miR-34a is a p53 Target That Induces Apoptosis and G1-arrest", *Cell Cycle*, 2007, vol. 6, No. 13, pp. 1586-1593.

Tazawa et al., "Tumor-suppressive miR-34a induces senescence-like growth arrest through modulation of the E2F pathway in human colon cancer cells", *PNAS*, 2007, vol. 104, pp. 15472-15477.

Raver-Shapira et al., "Transcriptional Activation of miR-34a Contributes to p53-Mediated Apoptosis", *Molecular Cell*, 2007, vol. 26, pp. 731-743.

Chen et al., "Lentivirus-Mediated RNA Interference Targeting Enhancer of Zeste Homolog 2 Inhibits Hepatocellular Carcinoma Growth Through Down-Regulation of Stathmin", *Hepatology*, 2007, vol. 46, No. 1, pp. 200-208.

Li et al., "Enhancer of Zeste Homolog 2 Silences MicroRNA-218 in Human Pancreatic Ductal Adenocarcinoma Cells by Inducing Formation of Heterochromatin", *Gastroenterology*, 2013, vol. 144, pp. 1086-1097.

Feng et al., "Tumor suppressor p53 meets microRNAs," *J. of Mol. Cell Biol.*, 2011, vol. 3, pp. 44-50.

Lee et al., "Phase II study of doxorubicin and cisplatin in patients with metastatic hepatocellular carcinoma", *Cancer Chemother. Pharmacol.*, 2004, vol. 54, pp. 385-390.

Llovet et al., "Sorafenib in Advanced Hepatocellular Carcinoma", *N. Engl. J. Med.*, 2008, vol. 359, pp. 378-390.

Lacouture et al., "Hand foot skin reaction in cancer patients treated with the multikinase inhibitors sorafenib and sunitinib", *Annals of Oncology*, 2008, vol. 19, pp. 1955-1961.

Kong et al., "Sorafenib-induced Eruptive Melanococytic Lesions", *Arch Dermatol.*, 2008, vol. 144, No. 6, pp. 820-822.

Zhao et al., "MicroRNA-34a induces endothelial progenitor cell senescence and impedes its angiogenesis via suppressing silent information regulator 1", *Am J. Physiol Endocrinol Metab*, 2010, vol. 299, pp. E110-E116.

Levine et al., "p53, the Cellular Gatekeeper for Growth and Division", *Cell*, 1997, vol. 88, pp. 323-331.

Hemlata, "Structural aspects in naturally occurring phenolics using $^1$H nmr acylation and alkoxylation shifts", *J Indian Inst. Sci*, vol. 72, pp. 15-22 (1992).

Office Action and Search Report dated May 18, 2015 for Chinese Patent Application No. 201310718172.8, with partial translation, 8 pages.

\* cited by examiner

A

B

C

D

Rubone(MW-374.39)
2'-Hydroxy-2,4,4',5,6'-pentamethoxychalcone

B

B

SEQUENCE LISTING

```
<160> NUMBER OF SEQ ID NOS: 35

<210> SEQ ID NO 1
<211> LENGTH: 24
<212> TYPE: DNA
<213> ORGANISM: Artificial Sequence
<220> FEATURE:
<223> OTHER INFORMATION: synthetic forward oligonucleotide DNA encoding
      miR-34a binding site, miRNA-34a binding site

<400> SEQUENCE: 1
ctggcagtgt cttagctggt tgta                                                24

<210> SEQ ID NO 2
<211> LENGTH: 32
<212> TYPE: DNA
<213> ORGANISM: Artificial Sequence
<220> FEATURE:
<223> OTHER INFORMATION: synthetic reverse oligonucleotide DNA encoding
      miR-34a binding site

<400> SEQUENCE: 2
```
agcttacaac cagctaagac actgccagag ct    32

<210> SEQ ID NO 3
<211> LENGTH: 21
<212> TYPE: DNA
<213> ORGANISM: Artificial Sequence
<220> FEATURE:
<223> OTHER INFORMATION: synthetic siRNA targeting p53
<220> FEATURE:
<223> OTHER INFORMATION: Description of Combined DNA/RNA Molecule:
      synthetic siRNA targeting p53

<400> SEQUENCE: 3
cuacuuccug aaaacaacgt t    21

<210> SEQ ID NO 4
<211> LENGTH: 20
<212> TYPE: DNA
<213> ORGANISM: Artificial Sequence
<220> FEATURE:
<223> OTHER INFORMATION: synthetic GAPDH endogenous control qRT-PCR
      amplification forward primer

<400> SEQUENCE: 4
tgcctcctgc accaccaact    20

<210> SEQ ID NO 5
<211> LENGTH: 20
<212> TYPE: DNA
<213> ORGANISM: Artificial Sequence
<220> FEATURE:
<223> OTHER INFORMATION: synthetic GAPDH endogenous control qRT-PCR
      amplification reverse primer

<400> SEQUENCE: 5
cccgttcagc tcagggatga    20

<210> SEQ ID NO 6
<211> LENGTH: 22
<212> TYPE: DNA
<213> ORGANISM: Artificial Sequence
<220> FEATURE:
<223> OTHER INFORMATION: synthetic p53 qRT-PCR amplification forward
      primer

<400> SEQUENCE: 6
cctcagcatc ttatccgagt gg    22

<210> SEQ ID NO 7
<211> LENGTH: 22
<212> TYPE: DNA
<213> ORGANISM: Artificial Sequence
<220> FEATURE:
<223> OTHER INFORMATION: synthetic p53 qRT-PCR amplification reverse
      primer

<400> SEQUENCE: 7
tggatggtgg tacagtcaga gc    22

<210> SEQ ID NO 8
<211> LENGTH: 22
<212> TYPE: DNA
<213> ORGANISM: Artificial Sequence
<220> FEATURE:
<223> OTHER INFORMATION: synthetic cyclin D1 qRT-PCR amplification
      forward primer

<400> SEQUENCE: 8
tctacaccga caactccatc cg                                          22

<210> SEQ ID NO 9
<211> LENGTH: 23
<212> TYPE: DNA
<213> ORGANISM: Artificial Sequence
<220> FEATURE:
<223> OTHER INFORMATION: synthetic cyclin D1 qRT-PCR amplification
      reverse primer

<400> SEQUENCE: 9
tctggcattt tggagaggaa gtg                                         23

<210> SEQ ID NO 10
<211> LENGTH: 22
<212> TYPE: DNA
<213> ORGANISM: Artificial Sequence
<220> FEATURE:
<223> OTHER INFORMATION: synthetic Bcl-2 qRT-PCR amplification forward
      primer

<400> SEQUENCE: 10
atcgccctgt ggatgactga gt                                          22

<210> SEQ ID NO 11
<211> LENGTH: 23
<212> TYPE: DNA
<213> ORGANISM: Artificial Sequence
<220> FEATURE:
<223> OTHER INFORMATION: synthetic Bcl-2 qRT-PCR amplification reverse
      primer

<400> SEQUENCE: 11
gccaggagaa atcaaacaga ggc                                         23

<210> SEQ ID NO 12
<211> LENGTH: 23
<212> TYPE: DNA
<213> ORGANISM: Artificial Sequence
<220> FEATURE:
<223> OTHER INFORMATION: synthetic CDK6 qRT-PCR amplification forward
      primer

<400> SEQUENCE: 12
ggataaagtt ccagagcctg gag                                         23

<210> SEQ ID NO 13
<211> LENGTH: 22
<212> TYPE: DNA
<213> ORGANISM: Artificial Sequence
<220> FEATURE:
<223> OTHER INFORMATION: synthetic CDK6 qRT-PCR amplification reverse
      primer

<400> SEQUENCE: 13
gcgatgcact actcggtgtg aa                                          22

<210> SEQ ID NO 14
<211> LENGTH: 22
<212> TYPE: DNA
<213> ORGANISM: Artificial Sequence
<220> FEATURE:
<223> OTHER INFORMATION: synthetic FOXP1 qRT-PCR amplification forward
      primer

<400> SEQUENCE: 14
caaagaacgc ctgcaagcca tg                                              22

<210> SEQ ID NO 15
<211> LENGTH: 23
<212> TYPE: DNA
<213> ORGANISM: Artificial Sequence
<220> FEATURE:
<223> OTHER INFORMATION: synthetic FOXP1 qRT-PCR amplification reverse
      primer

<400> SEQUENCE: 15
ggagtatgag gtaagctctg tgg                                             23

<210> SEQ ID NO 16
<211> LENGTH: 22
<212> TYPE: DNA
<213> ORGANISM: Artificial Sequence
<220> FEATURE:
<223> OTHER INFORMATION: synthetic Notch1 qRT-PCR amplification forward
      primer

<400> SEQUENCE: 16
ggtgaactgc tctgaggaga tc                                              22

<210> SEQ ID NO 17
<211> LENGTH: 22
<212> TYPE: DNA
<213> ORGANISM: Artificial Sequence
<220> FEATURE:
<223> OTHER INFORMATION: synthetic Notch1 qRT-PCR amplification reverse
      primer

<400> SEQUENCE: 17
ggattgcagt cgtccacgtt ga                                              22

<210> SEQ ID NO 18
<211> LENGTH: 22
<212> TYPE: DNA
<213> ORGANISM: Artificial Sequence
<220> FEATURE:
<223> OTHER INFORMATION: synthetic SiRT1 qRT-PCR amplification forward
      primer

<400> SEQUENCE: 18
tagacacgct ggaacaggtt gc                                              22

<210> SEQ ID NO 19
<211> LENGTH: 22
<212> TYPE: DNA
<213> ORGANISM: Artificial Sequence
<220> FEATURE:
<223> OTHER INFORMATION: synthetic SiRT1 qRT-PCR amplification reverse
      primer

<400> SEQUENCE: 19
ctcctcgtac agcttcacag tc                                              22

<210> SEQ ID NO 20
<211> LENGTH: 20
<212> TYPE: DNA
<213> ORGANISM: Artificial Sequence
<220> FEATURE:
<223> OTHER INFORMATION: synthetic pri-miR-34a qRT-PCR amplification
      forward primer

<400> SEQUENCE: 20
cgtcacctct taggcttgga                                                 20

```
<210> SEQ ID NO 21
<211> LENGTH: 20
<212> TYPE: DNA
<213> ORGANISM: Artificial Sequence
<220> FEATURE:
<223> OTHER INFORMATION: synthetic pri-miR-34a qRT-PCR amplification
      reverse primer

<400> SEQUENCE: 21
cattggtgtc gttgtgctct                                               20

<210> SEQ ID NO 22
<211> LENGTH: 20
<212> TYPE: DNA
<213> ORGANISM: Artificial Sequence
<220> FEATURE:
<223> OTHER INFORMATION: synthetic miR-34a promoter qRT-PCR
      amplification forward primer

<400> SEQUENCE: 22
gaggccctcg gactgggcgt                                               20

<210> SEQ ID NO 23
<211> LENGTH: 23
<212> TYPE: DNA
<213> ORGANISM: Artificial Sequence
<220> FEATURE:
<223> OTHER INFORMATION: synthetic miR-34a promoter qRT-PCR
      amplification reverse primer

<400> SEQUENCE: 23
ggactccccg gccatcgcga ccc                                           23

<210> SEQ ID NO 24
<211> LENGTH: 22
<212> TYPE: DNA
<213> ORGANISM: Artificial Sequence
<220> FEATURE:
<223> OTHER INFORMATION: synthetic miR-34a qRT-PCR amplification forward
      primer

<400> SEQUENCE: 24
tggcagtgtc ttagctggtt gt                                            22

<210> SEQ ID NO 25
<211> LENGTH: 23
<212> TYPE: DNA
<213> ORGANISM: Artificial Sequence
<220> FEATURE:
<223> OTHER INFORMATION: synthetic miR-145 qRT-PCR amplification forward
      primer

<400> SEQUENCE: 25
gtccagtttt cccaggaatc cct                                           23

<210> SEQ ID NO 26
<211> LENGTH: 22
<212> TYPE: DNA
<213> ORGANISM: Artificial Sequence
<220> FEATURE:
<223> OTHER INFORMATION: synthetic miR-7a qRT-PCR amplification
      forward primer

<400> SEQUENCE: 26
tgaggtagta ggttgtatag tt                                            22
```

<210> SEQ ID NO 27
<211> LENGTH: 21
<212> TYPE: DNA
<213> ORGANISM: Artificial Sequence
<220> FEATURE:
<223> OTHER INFORMATION: synthetic miR-192 qRT-PCR amplification forward
      primer

<400> SEQUENCE: 27
ctgacctatg aattgacagc c                                              21

<210> SEQ ID NO 28
<211> LENGTH: 25
<212> TYPE: DNA
<213> ORGANISM: Artificial Sequence
<220> FEATURE:
<223> OTHER INFORMATION: synthetic miR-215 qRT-PCR amplification forward
      primer

<400> SEQUENCE: 28
atgacctatg aattgattga cacac                                          25

<210> SEQ ID NO 29
<211> LENGTH: 25
<212> TYPE: DNA
<213> ORGANISM: Artificial Sequence
<220> FEATURE:
<223> OTHER INFORMATION: synthetic miR-21 qRT-PCR amplification forward
      primer

<400> SEQUENCE: 29
tagcttatca gactgatgat gttga                                          25

<210> SEQ ID NO 30
<211> LENGTH: 21
<212> TYPE: DNA
<213> ORGANISM: Artificial Sequence
<220> FEATURE:
<223> OTHER INFORMATION: synthetic miR-23a qRT-PCR amplification forward
      primer

<400> SEQUENCE: 30
atcacattgc cagggatttc c                                              21

<210> SEQ ID NO 31
<211> LENGTH: 22
<212> TYPE: DNA
<213> ORGANISM: Artificial Sequence
<220> FEATURE:
<223> OTHER INFORMATION: synthetic miR-29c qRT-PCR amplification forward
      primer

<400> SEQUENCE: 31
tagcaccatt tgaaatcggt ta                                             22

<210> SEQ ID NO 32
<211> LENGTH: 23
<212> TYPE: DNA
<213> ORGANISM: Artificial Sequence
<220> FEATURE:
<223> OTHER INFORMATION: synthetic miR-34c qRT-PCR amplification forward
      primer

<400> SEQUENCE: 32
aggcagtgta gttagcygat tgc                                            23

```
<210> SEQ ID NO 33
<211> LENGTH: 21
<212> TYPE: DNA
<213> ORGANISM: Artificial Sequence
<220> FEATURE:
<223> OTHER INFORMATION: synthetic miR-219 qRT-PCR amplification forward
      primer

<400> SEQUENCE: 33
tgattgtcca aacgcaattc t                                              21

<210> SEQ ID NO 34
<211> LENGTH: 15
<212> TYPE: DNA
<213> ORGANISM: Artificial Sequence
<220> FEATURE:
<223> OTHER INFORMATION: synthetic U6 internal control qRT-PCR
      amplification forward primer

<400> SEQUENCE: 34
cggcagcaca tatac                                                     15

<210> SEQ ID NO 35
<211> LENGTH: 20
<212> TYPE: DNA
<213> ORGANISM: Artificial Sequence
<220> FEATURE:
<223> OTHER INFORMATION: synthetic U6 internal control qRT-PCR
      amplification reverse primer

<400> SEQUENCE: 35
ttcacgaatt tgcgtgtcat                                                20
```

SMALL MOLECULE MODULATORS OF MICRORNA-34A

CROSS-REFERENCES TO RELATED APPLICATIONS

This application claims priority to U.S. Provisional Application No. 61/745,348, filed Dec. 21, 2012, the contents of which are hereby incorporated by reference in its entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 132-1.TXT, created on Jan. 21, 2014, 8,192 bytes, machine format IBM-PC, MS-Windows operating system, is hereby incorporated by reference in its entirety for all purposes.

BACKGROUND OF THE INVENTION

MicroRNAs play critical roles in various biological processes through regulating gene expression. Encoded by eukaryotic nuclear DNA, microRNAs are thought to function via base-pairing with complementary sequences within mRNA molecules. MicroRNAs can provide negative regulation (transcript degradation and sequestering, translational suppression) and positive regulation (transcriptional and translational activation) of gene activity or expression.

MicroRNAs are well conserved in eukaryotic organisms and are thought to be a vital and evolutionarily ancient component of genetic regulation. The human genome may encode over 1000 microRNAs, which may target about 60% of mammalian genes and are abundant in many human cell types.

Mammalian microRNAs typically exhibit only partial complementarity to their mRNA targets. This partial complementarity may enable combinatorial regulation of a large number of genes from a smaller number of microRNAs. Indeed, combinatorial regulation is a common feature of microRNA regulation; and, a given microRNA may have multiple different mRNA targets, while a given target might similarly be targeted by multiple microRNAs.

Aberrant expression of microRNAs has been well documented in a variety of cancers. For example, microRNAs can function to facilitate the effects of oncogenes or tumor suppressor genes. Accordingly, microRNAs represent promising therapeutic targets for cancer treatment, and there exists a need for providing molecules that are capable of modulating the level and/or activity of microRNAs for therapeutic purposes. The invention fulfills this and other related needs.

BRIEF SUMMARY OF THE INVENTION

The present invention provides method of inhibiting cell proliferation comprising contacting a cell with an effective amount of the following compound:

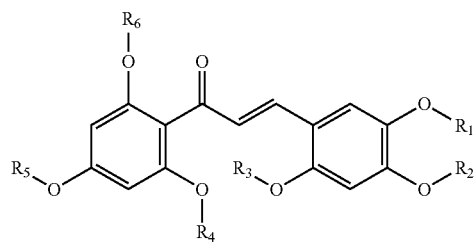

wherein $R_1$, $R_2$, $R_3$, $R_4$, $R_5$, $R_6$ are independently selected from the group consisting of H, $CH_3$, $CH_2CH_3$, F, Cl, Br, $NO_2$, OH, COOH, $NH_2$, $CF_3$, and CN.

In a further aspect, each of $R_1$-$R_5$ is $CH_3$, and $R_6$ is H.

In a further aspect, the cell is a cancer cell.

In a further aspect, the cancer cell comprises a hepatocarcinoma cell.

In a further aspect, the cell is an endothelial cell.

In a further aspect, the cell proliferation comprises angiogenesis.

In a further aspect, the cell is present in a patient.

In a further aspect, the contacting step comprises subcutaneous, intramuscular, intravenous, intraperitoneal, or oral administration of the foregoing compound. In some cases, the administration is to a subject in need thereof, such as a subject exhibiting a disease caused by cellular proliferation. In some cases, the disease caused by cellular proliferation is cancer. In some cases, the cancer is a carcinoma, such as an hepatocarcinoma.

In some cases, the method further comprises simultaneous, or sequential administration of a chemotherapeutic, an anti-inflammatory drug, an immunomodulator, an anti-nausea compound, or an anti-anemia drug, such as a drug that induces the production of red blood cells. For example, the anti-anemia drug can be erythropoietin.

In a further aspect, the method further comprises modulating miRNA-34a.

In a further aspect, the method further comprises activating miRNA-34a.

In a further aspect, the method further comprises down-regulating cyclinD1.

In a further aspect, the miRNA-34a activity or expression is increased at least 3-fold, or decreased to at least ⅓rd in comparison to a cell that has not been contacted.

In a further aspect, the step of modulating miRNA-34a is detected using a polynucleotide encoding a reporter gene.

In a further aspect, the polynucleotide encoding a reporter gene comprises a sequence encoding for a luciferase or a fluorescent protein.

In one embodiment, the invention provides a method comprising the following steps: (a) contacting a cell with a candidate compound, the cell containing an expression cassette comprising: (i) a polynucleotide sequence encoding a reporter gene operably linked to a 5' promoter that is active or inducible in the cell; and (ii) a polynucleotide sequence encoding an miRNA-34a binding site operably linked to and 3' of the reporter gene; (b) detecting the level of the reporter gene expression when the cell is placed under conditions permissible for the reporter gene expression; and (c) identifying the compound as an miRNA-34a activator when the level of reporter gene expression is decreased compared to the level of reporter gene expression in the absence of the compound, and identifying the compound as an miRNA-34a inhibitor when the level of reporter gene expression is increased compared to the level of reporter gene expression in the absence of the compound.

In a further aspect, the reporter gene is a luciferase or a fluorescent protein.

In a further aspect, the cell is a cancer cell.

In a further aspect, the miRNA-34a binding site comprises CTGGCAGTGTCTTAGCTGGTTGTA (SEQ ID NO:1).

In one embodiment, the invention provides an expression cassette comprising: (a) a polynucleotide sequence encoding a reporter gene operably linked to a 5' promoter that is active or inducible in a cell; and (b) a polynucleotide sequence encoding an miRNA-34a binding site operably linked to and 3' of the reporter gene.

In a further aspect, the cell is a cancer cell.

In a further aspect, the reporter gene is a luciferase or a fluorescent protein.

In a further aspect, the composition further comprises a test cell.

In a further aspect, the test cell is a cancer cell.

In a further aspect, the cancer cell is a hepatocarcinoma cell.

In another embodiment, the invention provides a composition comprising:
a compound of:

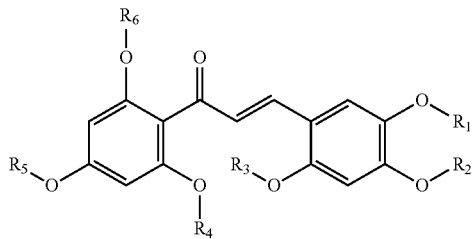

wherein $R_1$, $R_2$, $R_3$, $R_4$, $R_5$, $R_6$ are independently selected from the group consisting of H, $CH_3$, $CH_2CH_3$, F, Cl, Br, $NO_2$, OH, COOH, $NH_2$, $CF_3$, and CN; and a pharmaceutically acceptable excipient.

In one aspect, the composition further comprises an anti-anemia drug or an agent that promotes red blood cell production. For example, the composition can comprise erythropoietin. In some cases, the composition can comprise an anti-inflammatory, such as prednisone, or dexamethasone. In some cases, the composition can comprise a chemotherapeutic. In some cases, the composition can comprise an immunomodulator.

In another embodiment, the invention provides a kit for inhibiting proliferation of a cell, the kit comprising a composition comprising a compound of:

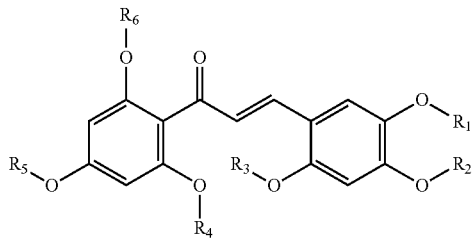

wherein $R_1$, $R_2$, $R_3$, $R_4$, $R_5$, $R_6$ are independently selected from the group consisting of H, $CH_3$, $CH_2CH_3$, F, Cl, Br, $NO_2$, OH, COOH, $NH_2$, $CF_3$, and CN; and a pharmaceutically acceptable excipient.

In a further aspect, the composition is formulated for subcutaneous, intramuscular, intravenous, intraperitoneal, topical, or oral administration.

The kit can further contain a detection reagent for detecting cellular proliferation. For example, the detection reagent for detecting cellular proliferation can be selected from the group consisting of CyQuant, CyQuant NF, CyQuant GR, (carboxyfluorescein succinimidyl ester, VPD450, bromodeoxyuridine, $^3$H-thymidine, 5-ethynyl-2'-deoxyuridine, sodium 2,3-bis(2-methoxy-4-nitro-5-sulfophenyl)-5-[(phenylamino)-carbonyl]-2H-tetrazolium salt, 3-(4,5-dimethyl-thiazol-2-yl)-2,5-diphenyltetrazolium bromide, [3-(4,5-dimethylthiazol-2-yl)-5-(3-carboxymethoxyphenyl)-2-(4-sulfophenyl)-2H-tetrazolium salt, and phenazine ethosulfate.

In some cases, the kit can contain an anti-anemia drug or an agent that promotes red blood cell production, such as erythropoietin. In some cases, the kit can contain an anti-inflammatory, such as prednisone, or dexamethasone. In some cases, the kit can contain a chemotherapeutic. In some cases, the kit can comprise an immunomodulator. In some cases, the kit can comprise an anti-nausea compound.

DETAILED DESCRIPTION OF THE INVENTION

I. Definitions

Figure 1:
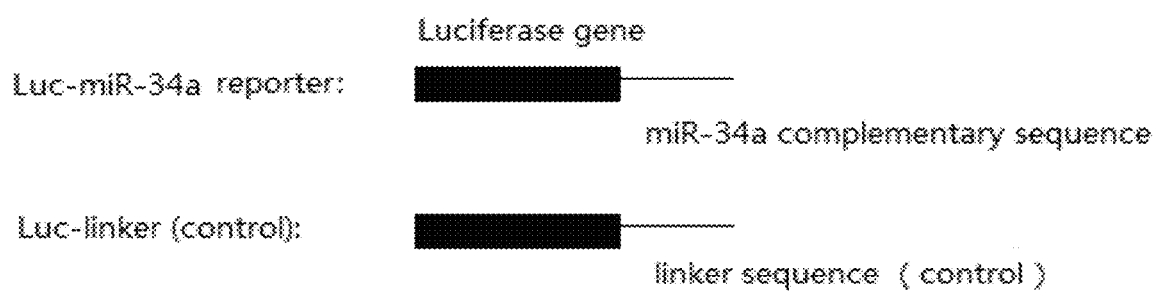
FIG. 1: Identification of miR-34a modulator through library screening. (A) Schematic illustration of miR-34a reporter system. The complementary sequences of mature miR-34a and control linker sequence were respectively introduced into pMIR-REPORT™ miRNA Reporter Vector (Ambion) to establish miR-34a reporter and control vectors. (B) Working mechanism of miR-34a reporter. miR-34a reporter could detect the presence of a functional mature miR-34a through repression of the luciferase signal. (C) The process of library screening for the identification of miR-34a modulators. (D) One small molecule compound named Rubone significantly inhibited the lucifierase activity of miR-34a reporter at a dose-dependent manner. Huh7 cells were transfected with miR-34a reporter and control vector and then treated with indicated concentrations of Rubone for 48 h. Cell lysates were subjected to luciferase assay. Results are expressed as luciferase activity values. The data are means and error bars representing 95% confidence intervals from three independent experiments.
Figure 1:
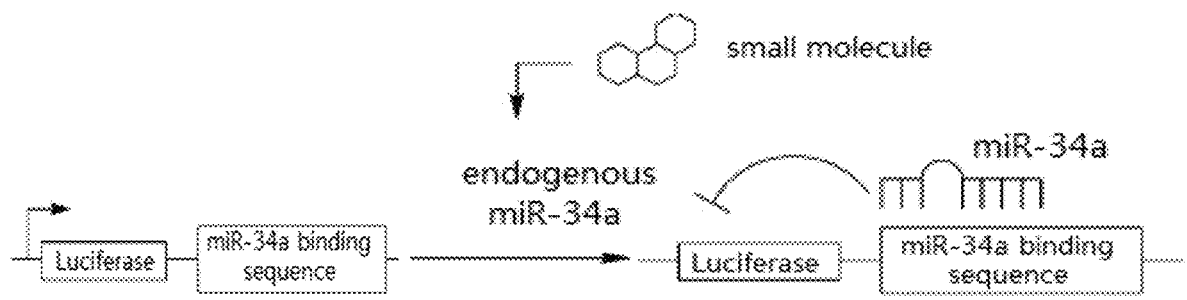
Figure 1:
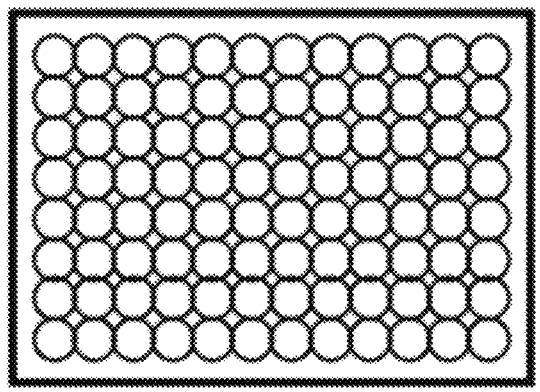
Figure 1:
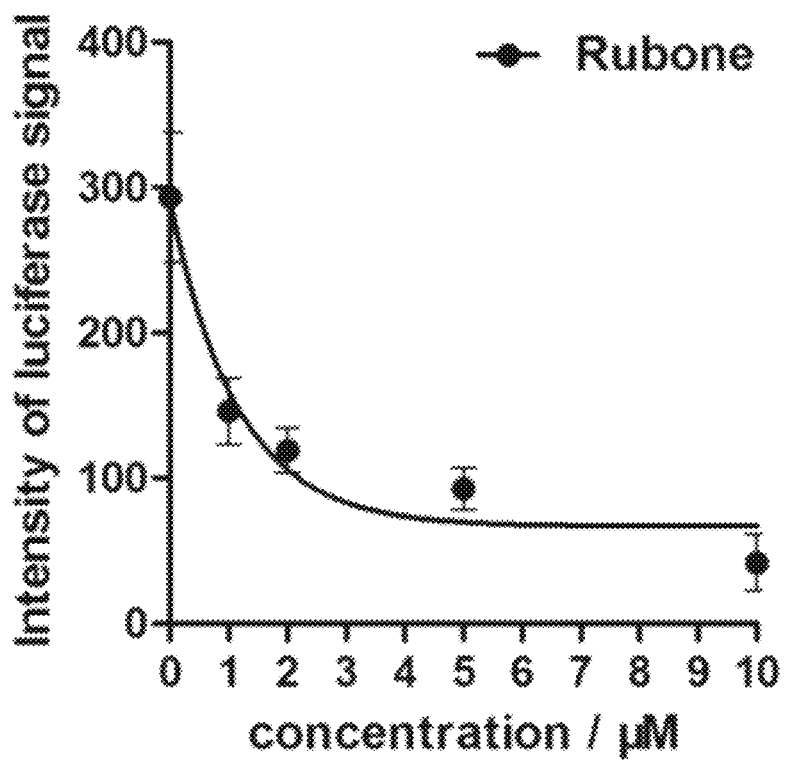
Figure 1:
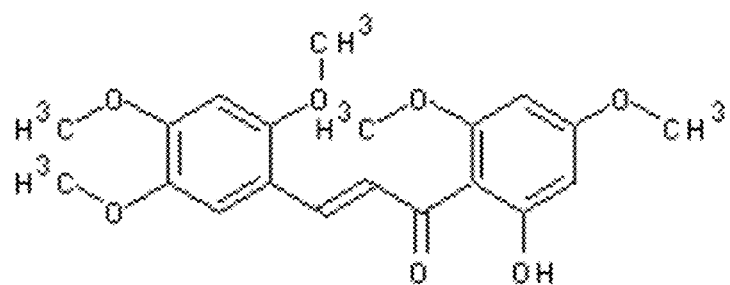

As used in this specification and the appended claims, the singular forms "a," "an," and "the" include plural reference unless the context clearly dictates otherwise.

As used herein "cancer" refers generally to one of a group of more than 100 diseases caused by the uncontrolled, abnormal growth of cells. Cancer cells can form a solid tumor, in which the cancer cells are massed together, or exist as dispersed cells, as in leukemia. In various embodiments "cancer" includes but is not limited to breast cancer, pancreatic cancer, cancer of the colon and/or rectum, leukemia, skin cancer, bone cancer, prostate cancer, liver cancer (e.g., hepatocarcinoma (HCC), lung cancer, brain cancer, or cancer of the larynx, gallbladder, parathyroid, thyroid, adrenal, neural tissue, head and neck, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, islet cell carcinoma, primary brain tumor, acute and chronic lymphocytic and granulocytic tumors, hairy-cell tumor, adenoma, hyperplasia, medullary carcinoma, pheochromocytoma, mucosal neuroma, intestinal ganglioneuroma, hyperplastic corneal nerve tumor, marfanoid habitus tumor, Wilm's tumor, seminoma, ovarian tumor, leiomyoma, cervical dysplasia and in situ carcinoma, neuroblastoma, retinoblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas.

The term "inhibiting" or "inhibition," as used herein, refers to any detectable negative effect on a target biological process, such as gene expression, protein activity, cellular signal transduction, cell proliferation, tumorigenicity, or metastatic potential. Typically, an inhibition is reflected in a decrease of at least 10%, 20%, 30%, 40%, or 50% in target process (e.g., miR-34a activity or cancer proliferation), or any one of the downstream parameters mentioned above, when compared to a control. In some cases, inhibition of miR-34a activity is provided by downregulation of pri-miRNA-34a expression or activity. In some cases, inhibition of miR-34a results in upregulation of cyclin D1, BCL-2, β-Klotho, MDM4, Notch1, Notch-2, and CDK6, Jagged1, Sirt1, survivin, Fra1, EphA5, YY1, FOxB1, MAPKK1, or c-Met expression or activity.

The term "activating" or "activation," as used herein, refers to any detectable positive effect on a target biological process, such as gene expression, protein activity, cellular signal transduction, cell proliferation, tumorigenicity, cyclin D1 activity, or metastatic potential. Typically, an activation is reflected in an increase of at least 10%, 20%, 30%, 40%, or 50% in target process (e.g., miR-34a activity or cancer proliferation), or any one of the downstream parameters mentioned above, when compared to a control. In some cases, activation of miR-34a activity results in downregulation of cyclin D1 or BCL-2 expression or activity. In some cases, activation of miR-34a activity is provided by upregulation of pri-miRNA-34a expression or activity.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

A "reporter gene" encodes proteins that are readily detectable due to their biochemical characteristics, such as enzymatic activity or chemifluorescent features. One specific example of such a reporter is green fluorescent protein. Fluorescence generated from this protein can be detected with various commercially-available fluorescent detection systems. Other reporters can be detected by staining. In some cases, the reporter is an enzyme that generates a detectable signal when contacted with an appropriate substrate. Often the reporter is an enzyme that catalyzes the formation of a detectable product. Suitable enzymes include, but are not limited to, proteases, nucleases, lipases, phosphatases and hydrolases. Typically, the reporter encodes an enzyme whose substrates are substantially impermeable to eukaryotic plasma membranes, thus making it possible to tightly control signal formation. Specific examples of suitable reporter genes that encode enzymes include, but are not limited to, CAT (chloramphenicol acetyl transferase; Alton & Vapnek (1979) Nature 282: 864-869); luciferase (lux); β-galactosidase; LacZ; β-glucuronidase; and alkaline phosphatase (Toh, et al. (1980) Eur. J. Biochem. 182: 231-238; and Hall et al. (1983) J. Mol. Appl. Gen. 2: 101), each of which are incorporated by reference herein in its entirety. Other suitable reporters include those that encode for a particular epitope that can be detected with a labeled antibody that specifically recognizes the epitope.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The terms "modulate," "modulation," "modify," "modulator," "modifier" and the like refer to the ability of a compound to increase or decrease the activity and/or expression of miR-34a, where such function may include transcription regulatory activity and/or nucleic acid-binding. Modulation may occur in vitro or in vivo. Modulation, as described herein, includes the inhibition, antagonism, partial antagonism, activation, agonism or partial agonism of a function or characteristic associated with miR-34a, either directly or indirectly, and/or the upregulation or downregulation of the expression of miR-34a, either directly or indirectly. In some cases, the modulation is direct. Inhibitors or antagonists are compounds that, e.g., bind to, partially or totally block, decrease, prevent, inhibit, delay activation, inactivate, desensitize, or downregulate miR-34a activity or expression. Activators or agonists are compounds that, e.g., bind to, stimulate, increase, activate, facilitate, enhance activation, sensitize or upregulate miR-34a activity or expression. The ability of a compound to modulate the function of miR-34a can be demonstrated in a biochemical assay, e.g., in a reporter gene assay.

The "subject" is defined herein to include animals such as mammals, including, but not limited to, primates (e.g., humans), cows, sheep, goats, horses, dogs, cats, rabbits, rats, mice and the like. In some embodiments, the subject is a human.

The terms "treat," "treating," "treatment" and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The term "effective amount," as used herein, refers to an amount that produces therapeutic effects for which a substance is administered. The effects include the prevention, correction, or inhibition of progression of the symptoms of a disease/condition and related complications to any detectable extent. The exact amount will depend on the nature of the therapeutic agent, the manner of administration, and the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

Compounds that have the same molecular formula but differ in the nature or sequence of bonding of their atoms or the arrangement of their atoms in space are termed "isomers." Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center(s) and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992).

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. These isomers can be resolved or asymmetrically synthesized using conventional methods to render the isomers "optically pure," i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

"Tautomer" refers to alternate forms of a molecule that differ in the position of a proton, such as enol-keto and imine-enamine tautomers, or the tautomeric forms of heteroaryl groups, such as pyrazoles, imidazoles, benzimidazoles, triazoles, and tetrazoles. A person of ordinary skill in the art would recognize that other tautomeric ring atom arrangements are possible.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," Journal of Pharmaceutical Science, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds that are in a prodrug ester form. "Prodrug"s of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, the term "chemotherapeutic" and the like refers to a drug or other compound for treatment of a disease. Chemotherapeutics include, but are not limited to, anticancer drugs. Exemplary chemotherapeutics include, inter alia, an 5-alpha-reductase inhibior such as finasteride, dutasteride, or izonsteride; a selective androgen receptor modulator, such as, RU-58642, RU-56279, WS9761 A or B, RU-59063, RU-58841, bexlosteride, LG-2293, L-245976, LG-121071, LG-121091, LG-121104, LGD-2226, LGD-2941, LGD-3303, YM-92088, YM-175735, LGD-1331, BMS-357597, BMS-391197, S-40503, BMS-482404, EM-4283, EM-4977, BMS-564929, BMS-391197, BMS-434588, BMS-487745, BMS-501949, GSK971086, GSK2420A, SA-766, YM-92088, YM-580, LG-123303, LG-123129, PMCol, YM-175735, BMS-591305, BMS-591309, BMS-665139, BMS-665539, CE-590, 116BG33, 154BG31, arcarine, or ACP-105; a selective estrogen receptor modulator, such as tamoxifen, 4-hydroxytamoxifen, idoxifene, toremifene, ospemifene, droloxifene, raloxifene, arzoxifene, bazedoxifene, PPT (1,3,5-tris(4-hydroxyphenyl)-4-propyl-1H-pyrazole), diarylpropionitrile (DPN), lasofoxifene, pipendoxifene, EM-800, EM-652, nafoxidine, zindoxifene, tesmilifene, miproxifene phosphate, RU 58,688, EM 139, ICI-164,384, ICI 182,780, clomiphene, MER-25, diethylstilbestrol, coumestrol, genistein, GW5638, LY353581, zuclomiphene, enclomiphene, delmadinone acetate, DPPE, (N,N-diethyl-2-{4-(phenylmethyl)-phenoxy}ethanamine), TSE-424, WAY-070, WAY-292, WAY-818, cyclocommunol, prinaberel, ERB-041, WAY-397, WAY-244, ERB-196, WAY-169122, MF-101, ERb-002, ERB-037, ERB-017, BE-1060, BE-380, BE-381, WAY-358, [18F]FEDNP, LSN-500307, AA-102, CT-101, CT-102, or VG-101; a gonadotropin-releasing hormone agonist or antagonist, such as, leuprolide, goserelin, triptorelin, alfaprostol, histrelin, detirelix, ganirelix, antide iturelix, cetrorelix, ramorelix, ganirelix, antarelix, teverelix, abarelix, ozarelix, sufugolix, prazarelix, degarelix, NBI-56418, TAK-810, or acyline; follicle stimulating hormone agonist/antagonist; leutenizing hormone agonist/antagonists, aromatase inhibitors, such as, letrozole, anastrazole, atamestane, fadrozole, minamestane, exemestane, plomestane, liarozole, NKS-01, vorozole, YM-511, finrozole, 4-hydroxyandrostenedione, aminogluethimide, or rogletimide; steroidal or nonsteroidal glucocorticoid receptor antagonists, agonists, or ligands, such as, prednisolone, methylprednisolone, prednisone, ZK-216348, ZK-243149, ZK-243185, LGD-5552, mifepristone, RPR-106541, ORG-34517, GW-215864X, sesquicillin, CP-472555, CP-394531, A-222977, AL-438, A-216054, A-276575, CP-394531, CP-409069, or UGR-07; steroidal or nonsteroidal progesterone receptor ligands; steroidal or nonsteroidal androgen receptor antagonists such as flutamide, hydroxyflutamide, bicalutamide, nilutamide, or hydroxysteroid dehydrogenase inhibitors; a PPARα ligand such as bezafibrate, fenofibrate, or gemfibrozil; a PPARδ ligand such as darglitazone, pioglitazone, rosiglitazone, isaglitazone, rivoglitazone, or netoglitazone; a dual acting PPAR ligand, such as naveglitazar, farglitazar, tesaglitazar, ragaglitazar, oxeglitazar, or PN-2034, PPARδ; a 17-ketoreductase inhibitor; a 3β-ΔHΔ4,6-isomerase inhibitor; a 3β-ΔHΔ4,5-isomerase inhibitora; a 17,20 desmolase inhibitor; a p450c17 inhibitor; a p450ssc inhibitor; a 17,20-lyase inhibitor; a DNA-modifying drug, such as cyclophosphamide, ifosfamide, cisplatin, carboplatin, carmustine, melphalan, or dacarbazine; an antimetabolite such as 5-fluorouracil, capecitabine, 6-mercaptopurine, methotrexate, gemcitabine, cytarabine, or fludarabine; a mitotic inhibitor, such as paclitaxel, docetaxel, vinblastine, or vincristine; an anthracyclines, such as daunorubicin, doxorubicin, epirubicin, idarubicin, or mitoxantrone; a topoisomerase I or II inhibitor, such as topotecan, irinotecan, etoposide, camptothecin, 7-ethyl-10-hydroxycamptothecin, or teniposide; a proteasome inhibitor such as bortezomib, carfilzomib, or MG132; interferon; a tyrosine kinase inhibitor, such as erlotinib, imatinib, gefitinib, ibrutinib, sorafenib, or sunitinib; a kinase inhibitor, such as the mTOR inhibitor sirolimus, everolimus, or temsirolimus; interferon-α2b; interleukin-2; a didemnin such as aplidine, or any combinations, isomers, or derivatives thereof.

As used herein, the term "immunomodulator" and the like refers to a compound which induces or inhibits an immune response. In some cases, the immunomodulator induces the production of one or more cytokines, e.g., Interferon (α), Tumor Necrosis Factor, or Interleukin 12, from hematopoietec cells including dendritic cells and/or monocyte/macrophages. Examples of such compounds include the CpG oligonucleotides, lipopolysaccharides, polyinosic:polycytidylic acid complexes, and polypeptides and proteins known to induce cytokine production from dendritic cells and/or monocyte/macrophages. Immunomodulators include, inter alia, cyclic peptides, such as cyclosporine, tacrolimus, tresperimus, pimecrolimus, sirolimus (rapamycin), verolimus, laflunimus, laquinimod and imidazoquinoline amines such as imiquimod. One of skill in the art will appreciate that other immunomodulators are useful in the present invention.

II. Introduction

MicroRNAs (miRNAs) are single-stranded noncoding RNAs of 21-23 nucleotides that regulate expression of many genes at the post-transcriptional level. miRNAs represent a new class of endogenous gene regulators that function by binding the 3' or 5' untranslated regions (UTRs) of target mRNAs leading to their regulation through suppression or activation of translation or degradation (Carthew et al.; He et al.; Lytle et al.).

Study of miRNA expression in cancer cells exhibits correlations between patterns of miRNA expression and cancer type, stage, and other clinical variables. This suggests that expression of miRNAs can be applied as a tool for cancer diagnosis and prognosis. This also suggests that miRNA may have oncogenic or tumor-suppressive roles. Indeed, miRNAs may play roles in almost all aspects of cancer biology, such as proliferation, apoptosis, invasion/metastasis, and angiogenesis. Given that many miRNAs are deregulated in cancers but have not yet been further studied, it is expected that more and more miRNAs will emerge as players in the etiology and progression of cancer.

The microRNA-34 family contains miR-34a, miR-34b and miR-34c. The miR-34 family members are all direct p53 targets, and their upregulation consistently induces cell apoptosis, cell-cycle arrest and senescence. Thus, activation of members of the miR-34 family, which induce the above-mentioned cellular responses, is advantageous for cancer therapy. For example, miR-34a acts as a tumor suppressor, its expression is highly down-regulated in cancer models such as human hepatocellular carcinoma (HCC) tissues, and it can inhibit migration and invasion in HCC cells (Welch et al.; Sun et al.; Li et al.). Therefore, activating miR-34a expression to reduce migration and invasion of cancer cells is a potential therapeutic modality.

Two small molecule inhibitors of miR-21 (Gumreddy, et al.), and inhibitors and activators of miR-122 have been reported (Young, et al.); however, no small molecule modifiers of miR-34a, which acts as an important tumor suppressive miRNA in many cancers (Bommer et al.; Chang et al.; He et al.; Tarasov et al.; Tazawa et al.; Raver et al.), have been reported. The present invention provides an assay for screening for small-molecule modifiers (e.g., activators and inhibitors) of miR-34a. The present invention also provides activators of miR-34a discovered from a natural product library (NPL, TimTec), and discloses their therapeutic potential against cancer cells in vitro and in vivo.

After a detailed screening of 640 compounds in Huh7 cells, two hit compounds Acacetin and Rubone are provided, the functions of these two compounds were re-assayed in triplicate with the miR-34a reporter system, and their functions as the miR-34a activators are confirmed. These compounds can produce a reduction in the intensity of a luciferase signal relative to that of untreated cells due to miR-34a activation. In some cases, these compounds can reduce the luciferase signal intensity to about $1/4^{th}$ or $1/6^{th}$ of the intensity in untreated cells. In some cases, these compounds can reduce the luciferase signal intensity to about $1/1000^{th}$, $1/500^{th}$, $1/250^{th}$, $1/100^{th}$, $1/75^{th}$, $1/50^{th}$, $1/25^{th}$, $1/12^{th}$, $1/10^{th}$, $1/9^{th}$, $1/8^{th}$, $1/7^{th}$, $1/6^{th}$, $1/5^{th}$, $1/4^{th}$, $1/3^{rd}$, or about one-half of the luciferase signal intensity in untreated control cells.

Acacetin (5,7-dihydroxy-4'-methoxyflavone) is a flavonoid compound broadly distributed in plants (Cody et al.), and exhibits crucial role in cancers exhibiting: antiperoxidative, anti-inflammatory, and antiplasmodial effects (Cholbi et al.; Liao et al.; Kraft et al); inhibition of invasion, migration, and proliferation; and induction of cell cycle arrest and apoptosis of various human cancer cells (Hsu et al. *Bioch. Pharm.*; Hsu et al. *Cancer Lett.*; Singh et al.; Pan et al.; Shim et al.; Shem et al.). However, the present invention elucidates the previously unknown relationship between Acacetin and miRNAs. Rubone (2'-Hydroxy-2,4, 4',5,6'-pentamethoxychalcone), is a compound that has not been previously reported to have any known biological activities. These compounds offer a new strategy for cancer treatment.

III. Identification of miR-34a Modifiers

Modifiers of miR-34a expression or activity can be of virtually any chemical or structural nature: they may be polypeptides, polynucleotides, and small molecules. As long as they possess a confirmed inhibitory or activating effect on miR-34a activity as a mediator of the expression of downstream targets, such modifiers may be useful for inhibiting cancer cell proliferation and therefore useful for treating cancer. For example, miR-34a activators may activate the expression of miR-34a, or activate the activity of miR-34a post-transcriptionally. Similarly, miR-34a inhibitors may inhibit the expression of miR-34a or inhibit the activity of miR-34a post-transcriptionally.

A. Reporter Gene Assay

An in vitro assay can be used to screen for potential modifiers of miR-34a signaling based on the interaction between a reporter gene and an miR-34a binding sequence. Candidate compounds may be screened by contacting a cell containing an expression cassette containing a reporter gene operably linked to an miR-34a binding sequence with the candidate compound. Modifiers can be identified as those compounds that upregulate or down regulate reporter gene activity as compared to control cells. For example, activators of miR-34a may be identified as compounds that down regulate reporter gene expression or activity. Similarly, inhibitors of miR-34a may be identified as compounds that upregulate reporter gene expression or activity. Once a compound is identified in the reporter gene assay, further testing may be conducted to confirm and verify the compounds capability of modifying miR-34a expression or activity. Such an assay can be performed in the presence of cells that endogenously produce miR-34a, in cells that express low levels of miR-34a, or in cells that do not generally produce miR-34a under conditions permitting miR-34a binding to an miR-34a binding sequence. For example, the screening may be performed in cancer cells, such as HCC cells, that downregulate miR-34a expression or activity.

In some cases, the miR-34a assays can be performed in a cell-free environment. For example, in an in vitro transcription translation system that includes an expression cassette containing a reporter gene operably linked to an miR-34a binding site.

B. Assay for Regulation of Downstream Targets

In some cases, modifiers of miR-34a activity or expression may be screened by screening for their effects on direct or indirect downstream targets. For example, activators of miR-34a may exhibit upregulation of pri-miRNA-34a or miR-34a expression or activity, or downregulation of cyclin D1 (Sun et al.), or BCL-2 (Cole et al.). Alternatively, inhibitors of miR-34a may exhibit downregulation of pri-miRNA-34a or miR-34a expression or activity, or upregulation of cyclin D1, BCL-2, β-Klotho, MDM4, Notch1, Notch-2, and CDK6, Jagged1, Sirt1, survivin, Fra1, EphA5, YY1, FOxB1, MAPKK1, or c-Met. Assays for confirming modulation of miR-34a by a candidate compound can be performed in vitro or in vivo. An in vitro assay typically involves exposure of cultured cells to an inhibitor and monitoring of subsequent biological and biochemical changes in the cells. For example, following exposure to a candidate compound at 10 μM for 0.5-48 hours, suitable cells (such as those that have downregulated miR-34a, e.g., HCC cells such as Huh7 or HepG2 cells) are examined for their proliferation/survival status using methods such as direct cell number counting, BrdU or $H^3$-thymidine incorporation, tetrazolium salt 3,[4,5-dimethylthiazol-2-yl]-2,5-diphenyltetrazolium bromide (MTT) cell proliferation assay, 3-(4,5-dimethylthiazol-2-yl)-5-(3-carboxymethoxyphenyl)-2-(4-sulfophenyl)-2H-tetrazolium (MTS) cell proliferation assay, chicken embryo allantoic membrane (CAM) assay, TUNNEL assay, annexin V binding assay, etc. Other downstream changes due to miR-34a modulation, e.g., pri-miR-34a expression, miR-34a expression, cyclin D1 expression, or BCL-2 expression can also be monitored, e.g., by quantitative RT-PCR (qPCR) or western blotting. In addition, tumorigenicity and/or metastatic potential of cancer cells may also be useful parameters for monitoring and can be tested by methods such as colony formation assays or soft agar assays. An effect is detected when change in miR-34a activity, as indicated by any one aforementioned parameters, of at least 10%, 20%, 30%, 40%, 50%, 60%, 70%, 80%, 90% or more is observed.

The anti-cancer effects of an miR-34a activator of the present invention can also be demonstrated in in vivo assays. For example, candidate activator can be injected into animals that have a compromised immune system (e.g., nude mice, SCID mice, or NOD/SCID mice) and therefore permit xenograft tumors. Injection methods can be subcutaneous, intramuscular, intravenous, intraperitoneal, or intratumoral in nature. Tumors development is subsequently monitored by various means, such as measuring tumor volume and scoring secondary lesions due to metastases, in comparison with a control group of animals with similar tumors but not given the inhibitor. The Examples section of this disclosure provides detailed description of some exemplary in vivo assays. An effect is detected when a negative effect on tumor growth or metastasis is established in the test group. Preferably, the negative effect on tumor growth is at least a 10% decrease; more preferably, the decrease is at least 20%, 30%, 40%, 50%, 60%, 70%, 80%, or 90%.

miR-34a activators can have diverse chemical and structural features. Essentially any chemical compound can be tested as a potential activator of miR-34a activity. Most preferred are generally compounds that can be dissolved in aqueous or organic (e.g., DMSO-based) solutions Inhibitors can be identified by screening a combinatorial library containing a large number of potentially effective compounds. Such combinatorial chemical libraries can be screened in one or more assays, as described herein, to identify those library members (particular chemical species or subclasses)

that display a desired characteristic activity. The compounds thus identified can serve as conventional "lead compounds" or can themselves be used as potential or actual therapeutics.

Preparation and screening of chemical libraries is well known to those of skill in the art. Such chemical libraries include, but are not limited to, natural product libraries. Natural product libraries are libraries of compounds that have been isolated from organisms (e.g., plants, microorganisms, cells, etc.) or other natural sources (e.g., soil, rock, etc.). In some cases, natural product libraries comprise a library of pure or substantially pure single compounds. In some cases, the structure and/or chemical formula of the compounds of the natural library are known. In other cases, the natural product library comprises a library of products that are not fully characterized, or have not been fully purified. For example, a natural product library may consist of various extracts (e.g., water extract, methanol extract, ethanol extract, DMSO extract, hexane extract, etc.) of various organisms (e.g., plants, plants, microorganisms, cells, etc.).

Chemical libraries may also include combinatorial chemical libraries. Preparation and screening of combinatorial chemical libraries is well known to those of skill in the art. Such combinatorial chemical libraries include, but are not limited to peptide libraries (see, e.g., U.S. Pat. No. 5,010,175, Furka, *Int. J. Pept. Prot. Res.* 37:487-493 (1991) and Houghton et al., *Nature* 354:84-88 (1991)) and carbohydrate libraries (see, e.g., Liang et al., *Science,* 274:1520-1522 (1996) and U.S. Pat. No. 5,593,853). Other chemistries for generating chemically diverse libraries can also be used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with β-D-glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see, Ausubel et al., *Current Protocols in Molecular Biology*, Greene Publishing Associates and John Wiley & Sons, New York, 1987, peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and benzodiazepines, U.S. Pat. No. 5,288,514).

IV. Compositions

The present invention provides compositions and compounds that modulate miR-34a activity (e.g., expression or binding to miR-34a binding sites). In some cases, compounds of the present invention activate miR-34a activity by increasing miR-34a expression or enhancing the binding of miR-34a to an miR-34a binding site. In other cases, compounds of the present invention inhibit miR-34a by decreasing miR-34a expression or inhibiting the binding of miR-34a to an miR-34a binding site. In some embodiments, compounds of the present invention that directly modulate miR-34a indirectly upregulate or downregulate expression of downstream targets due to their effect on miR-34a activity or expression. For example, activators of miR-34a may down regulate cycline D1, or BCL-2. In some cases, compounds of the present invention that modulate miR-34a activity are useful for treatment of diseases or conditions that involve rapidly dividing cells, including but not limited to cancer, such as hepatocarcinoma. For example, the present invention provides compounds of Formula I:

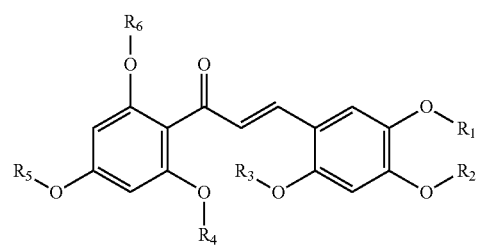

wherein $R_1$, $R_2$, $R_3$, $R_4$, $R_5$, $R_6$ are independently selected from the group consisting of H, $CH_3$, $CH_2CH_3$, F, Cl, Br, $NO_2$, OH, COOH, $NH_2$, $CF_3$, and, CN. In some cases, each of $R_1$-$R_5$ is $CH_3$, and $R_6$ is H.

V. Pharmaceutical Compositions and Administration

The present invention also provides pharmaceutical compositions or physiological compositions comprising an effective amount of a compound that modifies miR-34a activity or expression and therefore inhibits cancer development, e.g., an miR-34a activator. miR-34a modulators of the present invention include small chemicals, peptides, proteins, or natural products in both prophylactic and therapeutic applications. Such pharmaceutical or physiological compositions also include one or more pharmaceutically or physiologically acceptable excipients or carriers. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, subcutaneous, transdermal, intramuscular, intravenous, or intraperitoneal. Routes of administering the pharmaceutical compositions include local delivery to an organ or tissue suffering from a condition exacerbated by miR-34a down regulation (e.g., intratumor injection to a tumor) at daily doses of about 0.01-2500 mg, preferably 2.5-500 mg, of a miR-34a activator for a 70 kg adult human per day. The appropriate dose may be administered in a single daily dose or as divided doses presented at appropriate intervals, for example as two, three, four, or more subdoses per day.

For preparing pharmaceutical compositions containing a miR-34a modulator, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., Acacetin, Rubone, or a derivative thereof. In tablets, the active ingredient (e.g., an activator of miR-34a expression or activity) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient of a modulator of miR-34a activity. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an miR-34a modulator with encapsulating material as a carrier providing a capsule in which the modulator (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an miR-34a modulator such as an activator, including but not limited to Acacetin or Rubone or a derivative thereof), or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., a miR-34a modulator) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing an miR-34a modulator can be administered for prophylactic and/or therapeutic treatments. In therapeutic applications, compositions are administered to a patient already suffering from a condition that may be exacerbated by down regulation of miR-34a in an amount sufficient to prevent, cure, reverse, or at least partially slow or arrest the symptoms of the condition and its complications, such as the onset, progression, and metastasis of certain types of cancer. An amount adequate to accomplish this is defined as a "therapeutically effective dose." Amounts effective for this use will depend on the severity of the disease or condition and the weight and general state of the patient, but generally range from about 0.1 mg to about 2,500 mg of the inhibitor per day for a 70 kg patient, with dosages of from about 2.5 mg to about 500 mg of the inhibitor per day for a 70 kg patient being more commonly used.

In prophylactic applications, pharmaceutical compositions containing an miR-34a modulator (e.g., an activator or inhibitor of miR-34a expression or activity) are administered to a patient susceptible to or otherwise at risk of developing a disease or condition in which miR-34a down regulation is undesirable, in an amount sufficient to delay or prevent the onset of the symptoms. Such an amount is defined to be a "prophylactically effective dose." In this use, the precise amounts of the modulator again depend on the patient's state of health and weight, but generally range from about 0.1 mg to about 2,500 mg of the inhibitor for a 70 kg patient per day, more commonly from about 2.5 mg to about 500 mg for a 70 kg patient per day.

Single or multiple administrations of the compositions can be carried out with dose levels and pattern being selected by the treating physician. In any event, the pharmaceutical formulations should provide a quantity of modulator sufficient to effectively activate or inhibit miR-34a activity or expression in the patient, either therapeutically or prophylactically.

All patents, patent applications, and other publications, including GenBank Accession Numbers, cited in this application are incorporated by reference in the entirety for all purposes.

VI. EXAMPLES

The following examples are provided by way of illustration only and not by way of limitation. Those of skill in the art will readily recognize a variety of non-critical parameters that could be changed or modified to yield essentially the same or similar results.

Example 1

Materials and Methods

Reporter Plasmid Construction

The pMIR-REPORT™ luciferase plasmid (1 µg; Ambion) was sequentially double digested with Sac I and Hind III (10 units each, 50 µL reaction; NEB) and was gel purified. Double stranded insert DNA encoding the miR-34a binding site was synthesized through standard oligonucleotide synthesis methods. The sequences used were Forward: 5'-CTGGCAGTGTCTTAGCTGGTTGTA-3' (SEQ ID NO:1) and Reverse: 5': AGCTTACAACCAGCTAA-GACACTGCCAGAGCT-3' (SEQ ID NO:2). The insert was hybridized (heated to 95° C., and cooled to 4° C. over 30 min, then held at 4° C. for 60 min) and ligated with T4 ligase (200 units, 10 µL reaction, 1:10 vector/insert ratio; NEB) into the digested pMIR-REPORT™ luciferase vector. Positive colonies were selected by PCR colony screens, and the construction of the pMIR-REPORT™-miR-34a vector was confirmed by double enzyme digestion with NheI, MluI and Nhe I, Hind III (NEB). The luciferase reporter vector containing the miR-34a promoter was kindly provided by Prof. Mendell J T from Johns Hopkins University (21).

Cell Culture

Non-tumorigenic human hepatocyte cell line MIHA, and five HCC cell lines: HepG2, Huh7, Bel-7404, PLC/PRF/5 (PLC) and Hep3B were maintained in the inventors' lab (25). All the cells were cultured under the condition as previously described (25). Carboxymethylcellulose was provided by Unitech Chemicals (Zibo, China). Sorafenib was purchased from Bayer Healthcare (Germany). Dimethyl sulfoxide (DMSO), Cisplatin (CDDP), 5-Fluorouracil (5-FU) and Doxorubicin (Dox) were all purchased from Sigma (USA).

MiR-34a mimics duplex, single strand miR-34a inhibitors and siRNAs targeting p53 (5'-CUA CUU CCU GAA AAC AAC G dTdT-'3, SEQ ID NO:3) were purchased from Shanghai GenePharma Co. The miR-34a mimics, inhibitors and siRNAs were transfected into HCC cells using DharmaFECT siRNA transfection reagent (Thermo Scientific, Lafayette, Colo.) according to manufacturer's protocol. The plasmids referred in this study were transfected into HCC cells using Lipofectamin 2000 (Invitrogen) according to manufacturer's protocol.

Luciferase Assay

Huh7 cells were seeded into 96-well plates 12 h prior to transfection. MiR-34a reporter and the control vector were respectively co-transfected with Renilla luciferase pRL-SV40 into Huh7 cells. All transfections were performed in triplicate. The cells were incubated at 37° C. for 4 h followed by the replacement of transfection media with standard DMEM growth media with 10 µM of the natural products library (NPL) compounds (Tim Tec; 0.1% DMSO final concentration). This library contains 640 compounds including natural products and their derivatives. After 48 h of incubation, the media was removed and cells were lysed and the luciferase signals were measured by luciferase assay as described below.

MiR-34a reporter, the luciferase reporter vector containing miR-34a promoter and the control vectors were transfected into HCC cells 12 h before compound treatment. The Renilla luciferase vector pRL-SV40 was co-transfected as an internal control. HCC cells were then treated with compound for 48-72 h. The luciferase activity was measured by Dual Luciferase Reporter Assay (Promega) with a Wallac VICTOR³V luminometer. The ratio of firefly luciferase to Renilla expression was calculated for each of the triplicates.

Total RNA and Protein Extraction

Total RNA from cell cultures and HCC xenograft tumors were extracted using Trizol (Invitrogen) according to manufacturer's protocols. Total RNAs were dissolved into nuclease-free ddH2O. For protein extraction, cells and HCC xenograft tumors were lysed in 1×RIPA buffer with 1 mM PMSF and 1× complete protease inhibitor cocktail (Roche, Indianapolis, Ind.). Both RNA and protein were stored at −80° C.

Quantitative RT-PCR (qPCR)

Total RNA was reversely transcribed into cDNAs using High Capacity cDNA Reverse Transcription Kit (Applied Biosystems, Foster city, CA, USA) and nude RT kit (Invitrogen) individually. qRT-PCR was performed using SYBR Green PCR master mix (TaKaRa, Dalian, China). GAPDH was used as an endogenous control. For measuring miR-34a expression level, qPCR was performed by using SYBR Green PCR master mixture (Invitrogen) and U6 was used as the internal control. The primers for amplifying referred genes were listed in table 1. All samples were normalized to internal controls and fold changes were calculated by relative quantification ($2^{-\Delta\Delta Ct}$).

TABLE 1

| Primer | Sequence (SEQ ID NO:) | |
|---|---|---|
| GAPDH | Forward: 5'-TGCCTCCTGCACCACCAACT-3' | (4) |
|  | Reverse: 5'-CCCGTTCAGCTCAGGGATGA-3' | (5) |
| p53 | Forward: 5'-CCTCAGCATCTTATCCGAGTGG-3' | (6) |
|  | Reverse: 5'-TGGATGGTGGTACAGTCAGAGC-3' | (7) |
| cyclin D1 | Forward: 5'-TCTACACCGACAACTCCATCCG-3' | (8) |
|  | Reverse: 5'-TCTGGCATTTTGGAGAGGAAGTG-3' | (9) |
| Bcl-2 | Forward: 5'-ATCGCCCTGTGGATGACTGAGT-3' | (10) |
|  | Reverse: 5'-GCCAGGAGAAATCAAACAGAGGC-3' | (11) |
| CDK6 | Forward: 5'-GGATAAAGTTCCAGAGCCTGGAG-3' | (12) |
|  | Reverse: 5'-GCGATGCACTACTCGGTGTGAA-3' | (13) |
| FOXP1 | Forward: 5'-CAAAGAACGCCTGCAAGCCATG-3' | (14) |
|  | Reverse: 5'-GGAGTATGAGGTAAGCTCTGTGG-3' | (15) |
| Notch1 | Forward: 5'-GGTGAACTGCTCTGAGGAGATC-3' | (16) |
|  | Reverse: 5'-GGATTGCAGTCGTCCACGTTGA-3' | (17) |
| SiRT1 | Forward: 5'-TAGACACGCTGGAACAGGTTGC-3' | (18) |
|  | Reverse: 5'-CTCCTCGTACAGCTTCACAGTC-3' | (19) |
| pri-miR-34a | Forward: 5'-CGTCACCTCTTAGGCTTGGA-3' | (20) |
|  | Reverse: 5'-CATTGGTGTCGTTGTGCTCT-3' | (21) |
| miR-34a promoter | Forward: 5'-GAGGCCCTCGGACTGGGCGT-3' | (22) |
|  | Reverse: 5'-GGACTCCCCGGCCATCGCGACCC-3' | (23) |
| miR-34a | Forward: 5'-TGGCAGTGTCTTAGCTGGTTGT-3' | (24) |
| miR-145 | Forward: 5'-GTCCAGTTTTCCCAGGAATCCCT-3' | (25) |
| miR-7a | Forward: 5'-TGAGGTAGTAGGTTGTATAGTT-3' | (26) |
| miR-192 | Forward: 5'-CTGACCTATGAATTGACAGCC-3' | (27) |
| miR-215 | Forward: 5'-ATGACCTATGAATTGATTGACACAC-3' | (28) |
| miR-21 | Forward: 5'-TAGCTTATCAGACTGATGATGTTGA-3' | (29) |
| miR-23a | Forward: 5'-ATCACATTGCCAGGGATTTCC-3' | (30) |
| miR-29c | Forward: 5'-TAGCACCATTTGAAATCGGTTA-3' | (31) |
| miR-34c | Forward: 5'-AGGCAGTGTAGTTAGCYGATTGC-3' | (32) |
| miR-219 | Forward: 5'-TGATTGTCCAAACGCAATTCT-3' | (33) |
| U6 | Forward: 5'-CGGCAGCACATATAC-3' | (34) |
|  | Reverse: 5'-TTCACGAATTTGCGTGTCAT-3' | (35) |

Western Blotting

Protein quantification was performed using BCA protein assay kit (Thermo Fisher Scientific, Rockford, Ill., USA). 25-50 µg protein was separated by SDS-PAGE (sodium dodecyl sulfate-polyacrylamide gel electrophoresis) and transferred to PVDF membranes (Bio-Rad). Primary antibodies used in this study included anti-cyclinD1 (1:1000 dilution), anti-BCL2 (1:1000 dilution), β-actin (1:5000) and anti-p53 (all from Cell Signaling Technology, Beverly, Mass., USA). Membranes were incubated with primary antibody at 4° C. overnight, and then washed thrice with TBST (Tris-Buffered Saline Tween-20). The membranes were then incubated with 1:3000 peroxidase conjugated secondary antibody (Santa Cruz) for 1 h at room temperature, followed by three washings in TBST. Protein expression was detected by autoradiography using Amersham ECL Plus™ Western Blotting Detection Reagents (GE Healthcare, Uppsala, Sweden).

In Vivo HCC Xenografted Mouse Model $5 \times 10^6$ HepG2 cells were suspended in 100 μl serum-free medium and subcutaneously (s.c.) inoculated into the dorsal flanks of nude mice. When tumors reached 5-10 mm in diameter, mice were randomly divided into 4 groups (n=5). Rubone and Sorafenib were suspended in a carboxymethylcellulose vehicle formulation, which contained 0.4% carboxymethylcellulose sodium and 0.9% NaCl. Tumor bearing mice were treated with 20 mg/kg or 50 mg/kg Rubone in 200 μl vehicle by gavages once every two days. Vehicle alone and Sorafenib were used as the negative and positive control respectively. Tumor volumes and body weight were measured once every two days. Tumor volume was calculated as [(Length×Width×Height)±2]. Treatment was continued for 24 d. Finally, all mice were sacrificed and tumors were excised. Tumor weight was recorded. Tumor tissue was stored and prepared for subsequent RNA extraction or tissue sectioning. All animal experiments were approved by the Animal Experimental Ethics Committee of the Chinese University of Hong Kong.

In Vitro Tube Formation Assay

The in vitro tube formation assay with human umbilical vein endothelial cells (HUVECs) was performed using the in vitro Angiogenesis Assay Kit (Cell Biolabs). HUVECs were plated at the density of $2 \times 10^4$/well and treated with Dimethyl sulfoxide (DMSO) or Rubone (1 μm or 2 μM) respectively for 24 h. HUVECs were then seeded onto the ECM gel surface and cultured for 4 h. Then, 100 μl 1× Staining Solution was applied to each well and incubated 30 min at 37° C. and images were captured with an Olympus SC35 camera (Olympus America, Inc., Melville, N.Y.). Tube formation was quantified by counting the number of branching points on each image.

Cell Viability Assay

Cell viability was measured by 3-(4,5-Dimethylthiazol-2-yl)-2,5-diphenyltetrazolium bromide (MTT) assay. $1 \times 10^3$ Cells were seeded in triplicate on a 96 well plate and were allowed to grow for indicated time points. At each time point a set of cells were incubated with 0.5 mg/ml MTT diluted in 1×PBS. After 2 to 4 h incubation, the MTT solution was removed. The insoluble MTT was dissolved in DMSO. Absorbance at 570 nm was measured by an ELISA plate reader.

Immunohistochemical Staining

Immunohistochemical staining was performed on HepG2 xenografted tumor tissues with CD31 specific antibody (Cat #: Y059114, Abcam, Cambridge, Mass.). Subcutaneous tumor tissue sections were incubated with anti-CD31 overnight at 4° C. Mean microvessel density was calculated by averaging vessel counts from three random fields per slide.

Chromatin Immunoprecipitation (ChIP) Assay

ChIP assay was performed as described before (26). Cross-linked chromatin were incubated overnight with anti-H3 (Cat #: 9003, Cell Signaling Technology), IgG (Cat #: 9003, Cell Signaling Technology), p53 (Cat #: sc-106, Santa Cruz, Cambridge, Mass.). The precipitated DNA were quantitated absolutely by real-time PCR and normalized by respective 2% input.

Statistical Analysis

GraphPad Prism 5 (GraphPad Software, La Jolla, Calif.) was used for statistical analysis. Four-parameter logistic model was applied to calculate $IC_{50}$. Two tailed Student's t test was applied for data analysis. Data were presented as mean±95% confidence interval (CI). P values less than 0.05 were considered statistically significant.

Results

Identification of a Small Molecule Modulator of miR-34a by Library Screening

Figure 2:
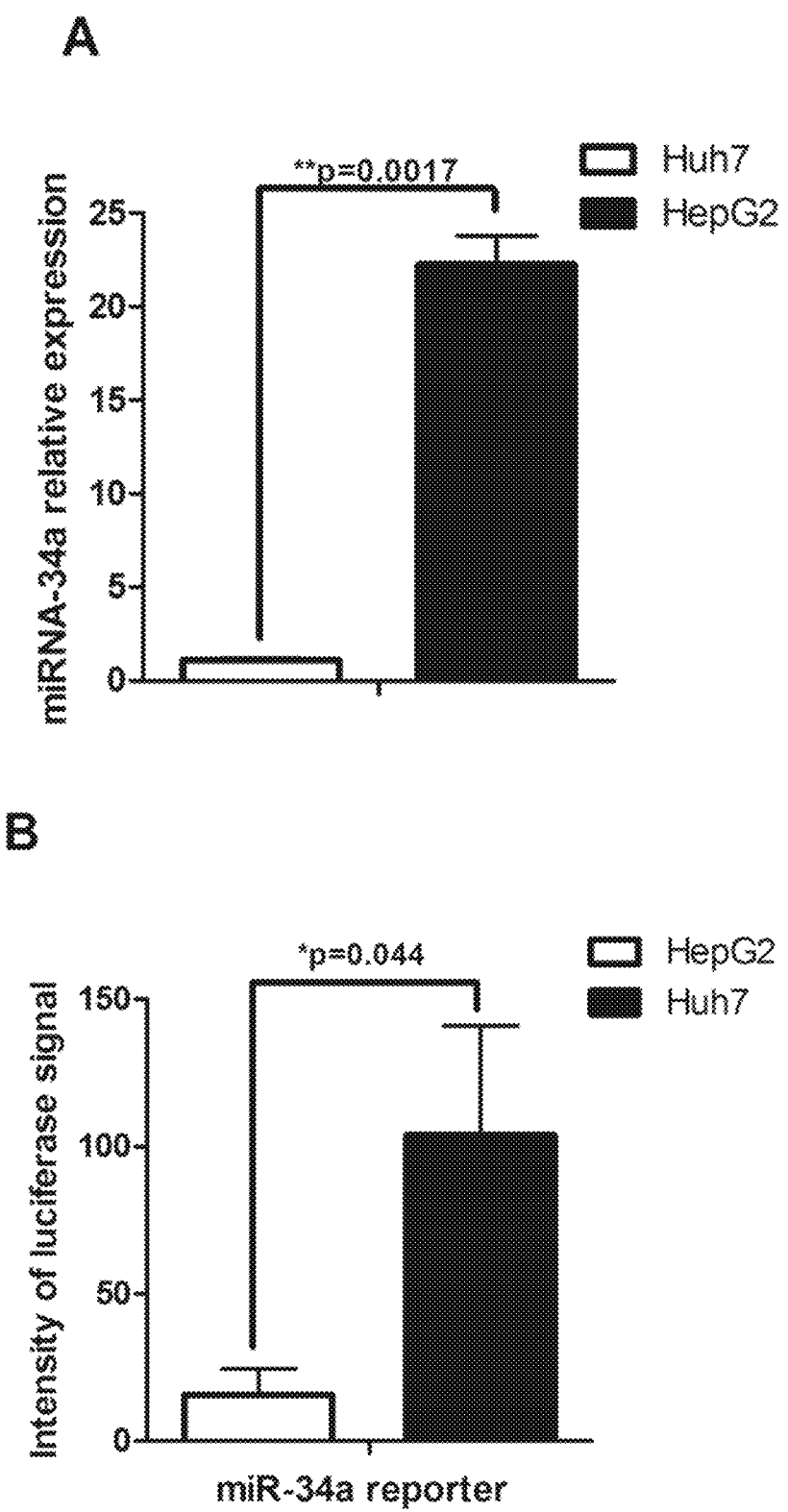
FIG. 2: The established miR-34a reporter was responsive to the endogeneous miR-34a level. (A) qRT-PCR was employed to quantify miR-34a expression levels in Huh7 and HepG2 cell lines. MiR-34a level in HepG2 cells was significantly higher than that in Huh7 cells. (B) MiR-34a reporter was transfected into HepG2 and Huh7 cells and the luciferase activity was measured. The luciferase activity in Huh7 cells was much higher than that of HepG2 cells. The means and error bars represent 95% confidence intervals from three independent experiments.

The inventors first established a luciferase reporter by cloning the complementary sequence of miR-34a into pmiR-Reporter vector (FIG. 1A). This miR-34a reporter could be used for screening miR-34a modulators by measuring luciferase signals (FIG. 1B). The endogenous miR-34a level in HepG2 cells was significantly higher (22.29-fold, p=0.0017) than that of Huh7 cells as measured by qRT-PCR (FIG. 2A). The inventors transfected miR-34a reporter into HepG2 and Huh7 cells respectively and measured the luciferase activities. The luciferase activities in Huh7 cells was significantly higher (15.66-fold, p=0.044) than that of HepG2 cells (FIG. 2B). These results indicated that miR-34a reporter was responsive to the endogenous miR-34a level.

With this miR-34a-Reporter system, the inventors screened a natural product library to identify small molecule miR-34a modulators using Huh7 cells. The screening process was depicted in FIG. 1C. After a primary screen of 640 compounds in Huh7 cells, one hit compounds named Rubone was discovered as a potential miR-34a modulator. Rubone was re-assayed in triplicate with the miR-34a reporter system. FIG. 1D showed Rubone inhibited the luciferase activities in a dose-dependent manner. Its calculated IC50 value was 3.8 μM. The chemical structure of Rubone is shown in FIG. 1D and its molecular weight is 374.39.

Figure 3:
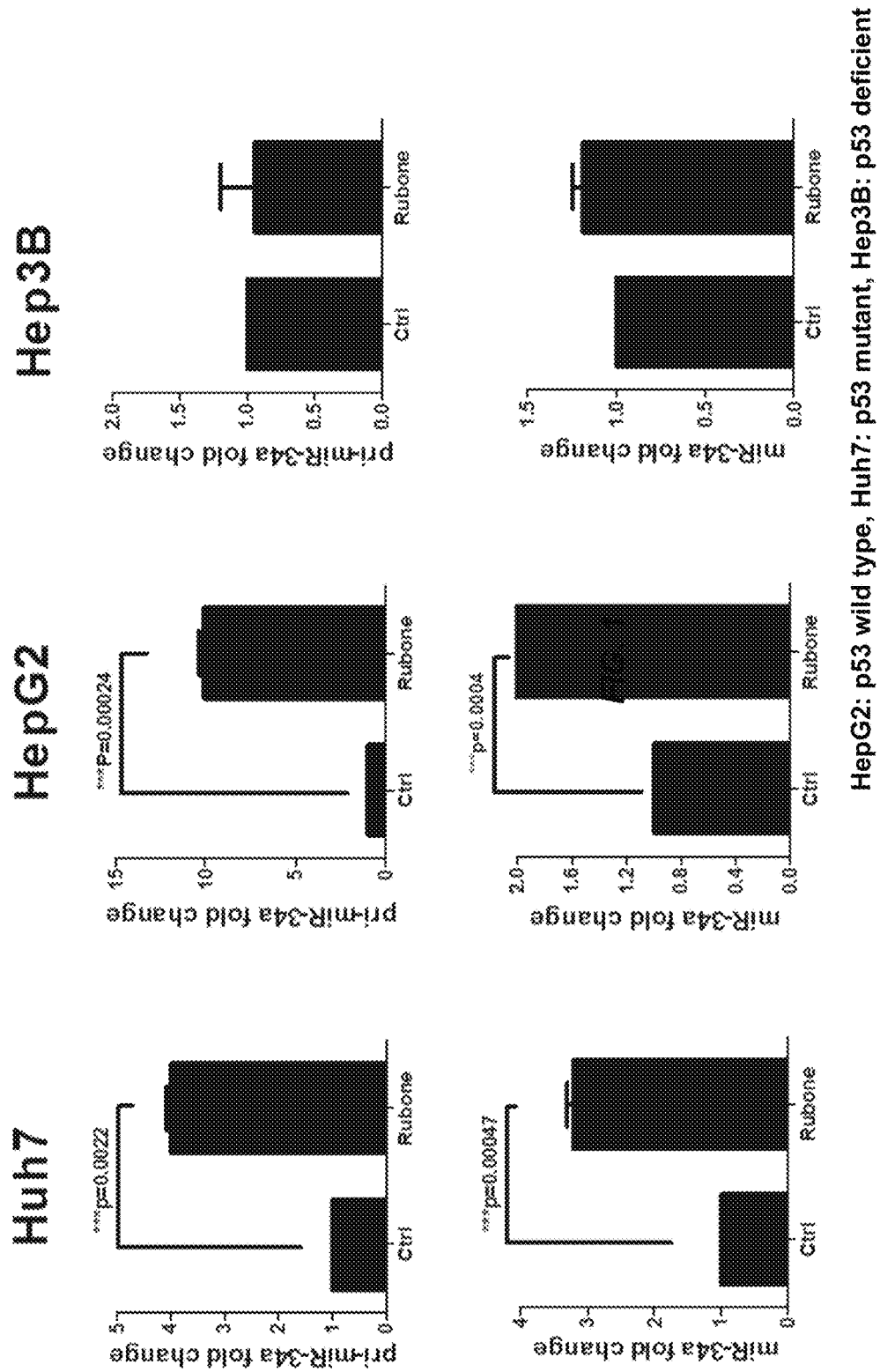
FIG. 3: Rubone increased miR-34a expression levels in HCC cells. Huh7, HepG2 and Hep3B cells were treated with Rubone at the concentration of 10 μM or vehicle control for 48 h. Then RNA samples were prepared and the fold changes of primary and mature miR-34a levels were measured by qRT-PCR. The means and error bars represent 95% confidence intervals from three independent experiments.

The inventors next examined whether Rubone could modulate miR-34a expression in HCC cells. As shown in FIG. 3, both primary and mature miR-34a levels significantly increased after treatment with Rubone in Huh7 and HepG2 cells. However, Rubone treatment caused no change in the expression levels of primary and mature miR-34a in Hep3B cells (FIG. 3). Huh7 cells expressed mutant p53 while HepG2 cells contain wild-type p53. However, p53 was deleted in Hep3B cells. These results indicated that Rubone dramatically modulated miR-34a expression in HCC cells expressing either wild-type or mutant p53 but not in HCC cells with p53 deletion.

Figure 4:
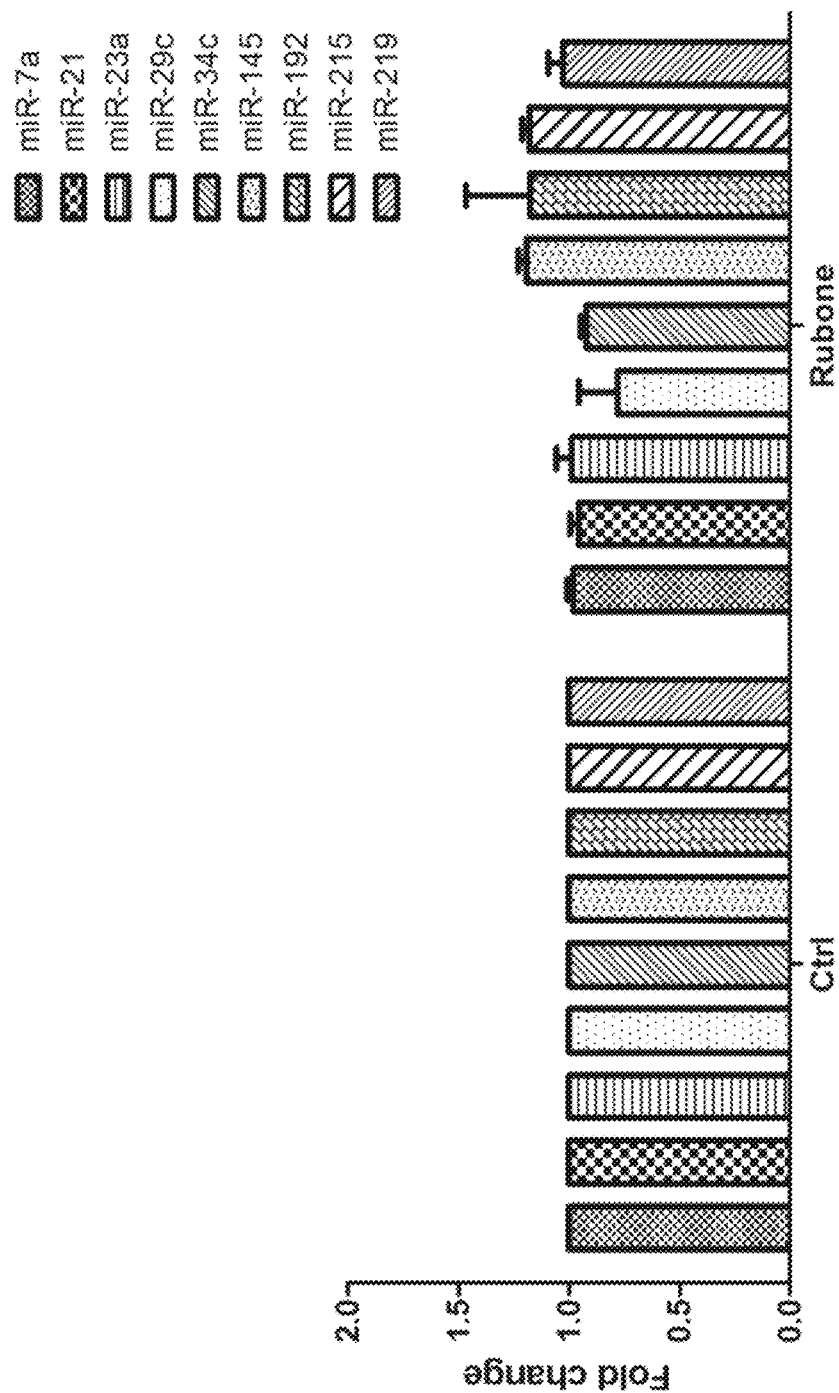
FIG. 4: Rubone specific activated the expression of miR-34a. (A) The Huh7 cells were treated with 10 μM Rubone for 48 h. RNA samples were prepared and qRT-PCR was applied to measure the levels of a randomly selected panel of miRNAs (miR-7a, miR-21, miR-29c, miR-34c, miR-219) and p53 regulated miRNAs (miR-34c, miR-145, miR-192, miR-215). Rubone caused no change in the expression of the selected miRNAs. (B) HepG2 cells were treated with the commonly used anti-cancer drugs: 5-Fluorouracil (5-FU); Cisplatin (CDDP); Doxorubicin (DOX) and Sorafenib. The levels of the pri-miR-34a and mature miR-34a were measured by qRT-PCR. Error bars=95% confidence intervals from three independent experiments. (C) Rubone decreased the expression of miR-34a targets by qRT-PCR. Huh7, HepG2 and Hep3B cells were treated with Rubone at the concentration of 10 μM or vehicle control for 48 h. RNA samples collected at 48 h were applied for measuring miR-34a targets CDK6, FOXP1, Noctch1, SIRT1 and by qRT-PCR. The means and 95% confidence intervals (error bars) are presented from three independent experiments. P values were calculated using a two-sided Student's t test.
Figure 4:
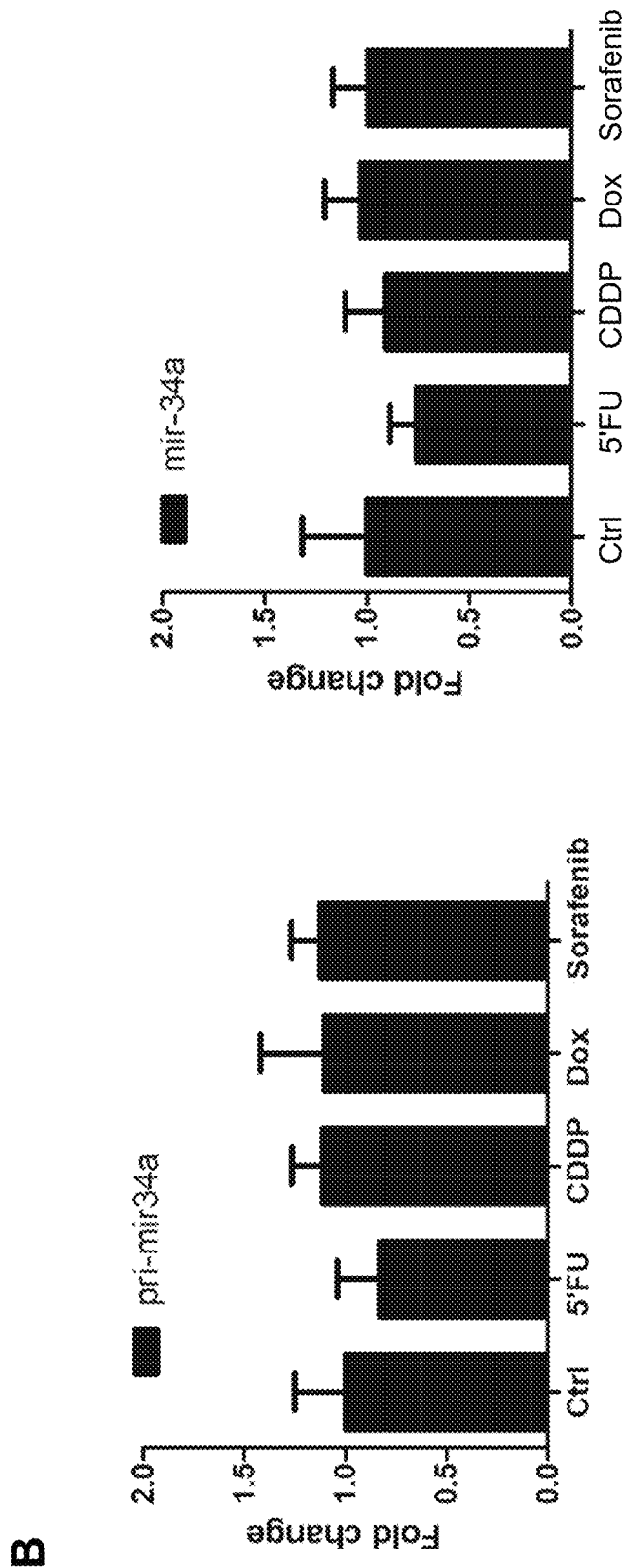
Figure 4:
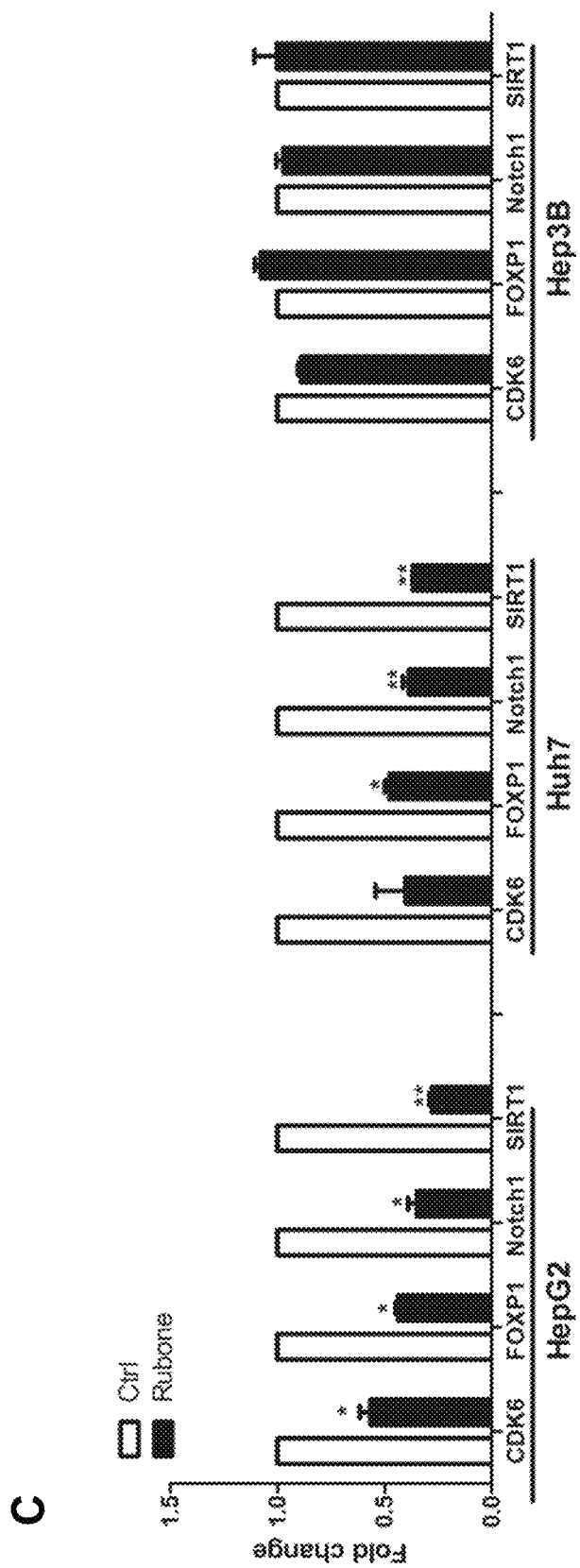
Figure 5:
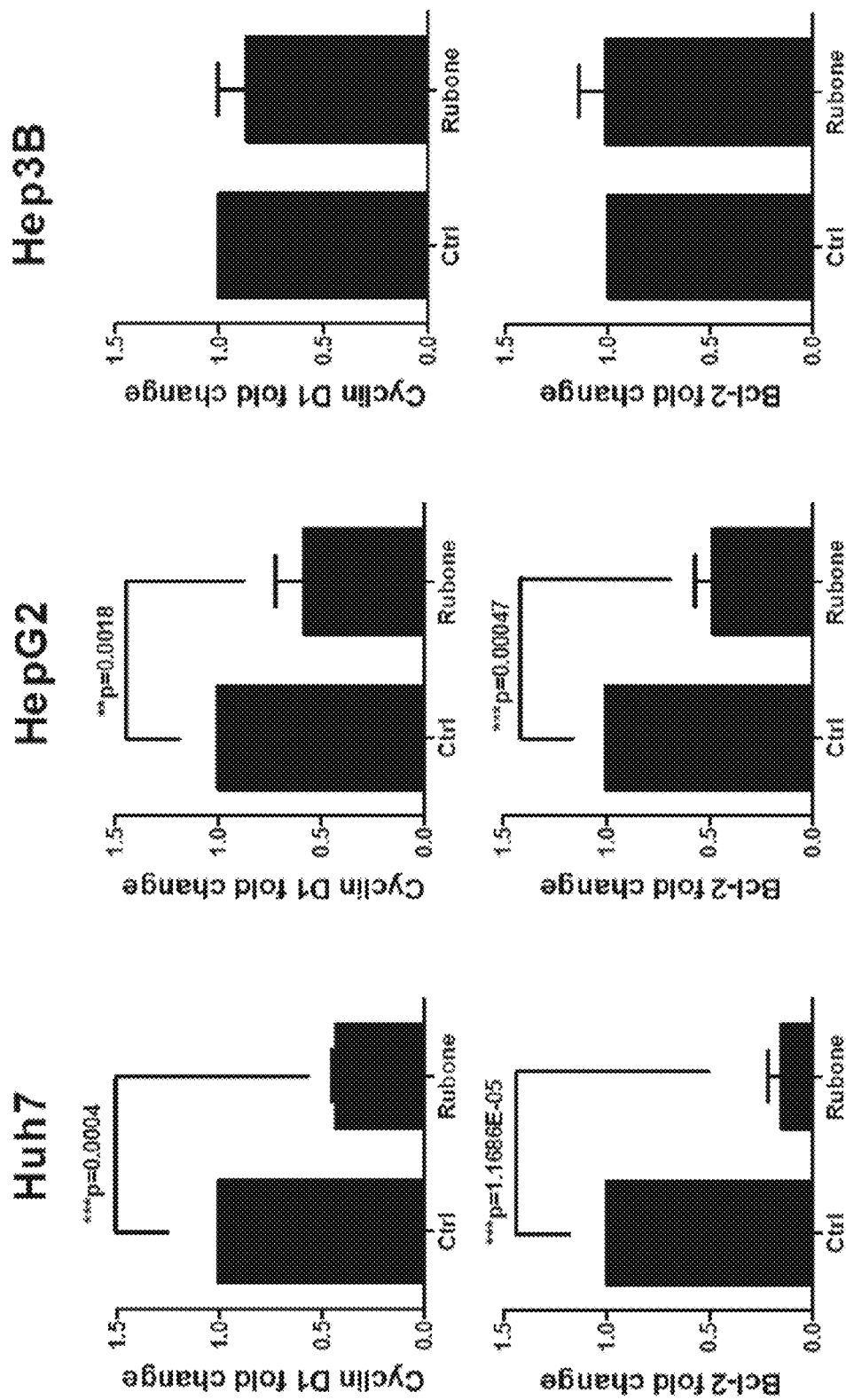
FIG. 5: Rubone decreased the expression of miR-34a targets. Huh7, HepG2 and Hep3B cells were treated with Rubone at the concentration of 10 μM or vehicle control for 48 h or 72 h. RNA samples collected at 48 h were applied for measuring miR-34a targets cyclin D1 and Bcl2 by qRT-PCR. The means and 95% confidence intervals (error bars) are presented from three independent experiments. P values were calculated using a two-sided Student's t test. The cell lysates collected at 72 h were subjected to western blotting. Specific antibodies against cyclin D1 (1:2500 dilution), Bcl-2 (1:2500 dilution) and β-actin (1:5000 dilution) were used.
Figure 5:
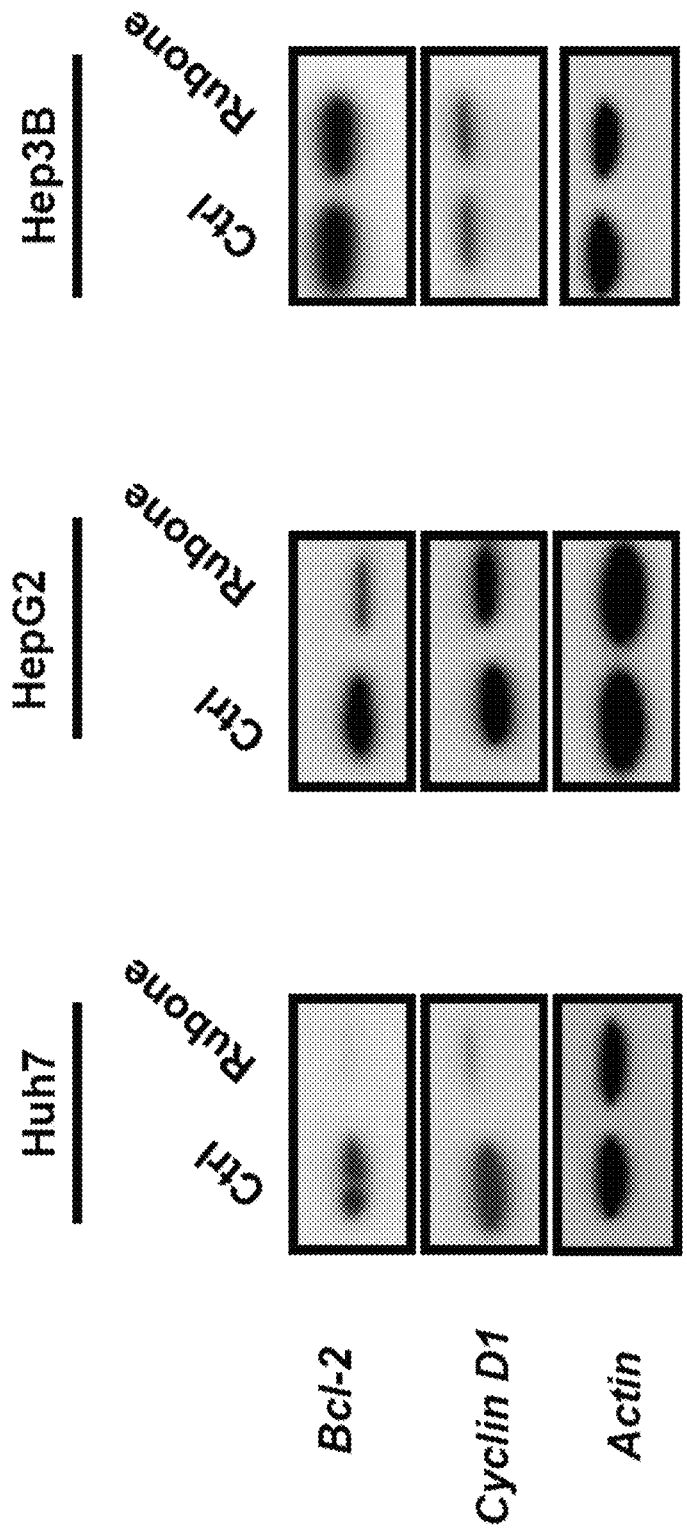

To exclude the possibility of non-specific modulation on miR-34a expressions by Rubone, we randomly measured a panel of intracellular microRNAs. Results showed the expressions of miR-7a, miR-21, miR-23a, miR-29c, miR-34c and miR-219 were not affected upon treatment with Rubone (FIG. 4A). We further demonstrated that other chemotherapeutic drugs Cisplatin (CDDP), 5-Fluorouracil (5-FU), Doxorubicin (Dox) and Sorafenib had no effect on miR-34a expression in HCC cells (FIG. 4B). These results indicated that Rubone specifically and dramatically modulated miR-34a expression in HCC cells. Cyclin D1 and Bcl-2 were two of the most well studied miR-34a targets with important roles in HCC. We examined the expression levels of Cyclin D1 and Bcl-2 after Rubone treatment. Rubone significantly reduced the mRNA and protein levels of Cyclin D1 and Bcl-2 in Huh7 and HepG2 cells but not in Hep3B cells (FIG. 5). Meanwhile, we measured the expression levels of other miR-34a targets including CDK6, FOXP, Notch1 and Sirtuin. Similarly, the expression levels of these targets were decreased after treatment with this compound in Huh7 and HepG2 but not in Hep3B cells (FIG. 4C).

MiR-34a Modulator Inhibited HCC Cell Growth In Vitro

Figure 6:
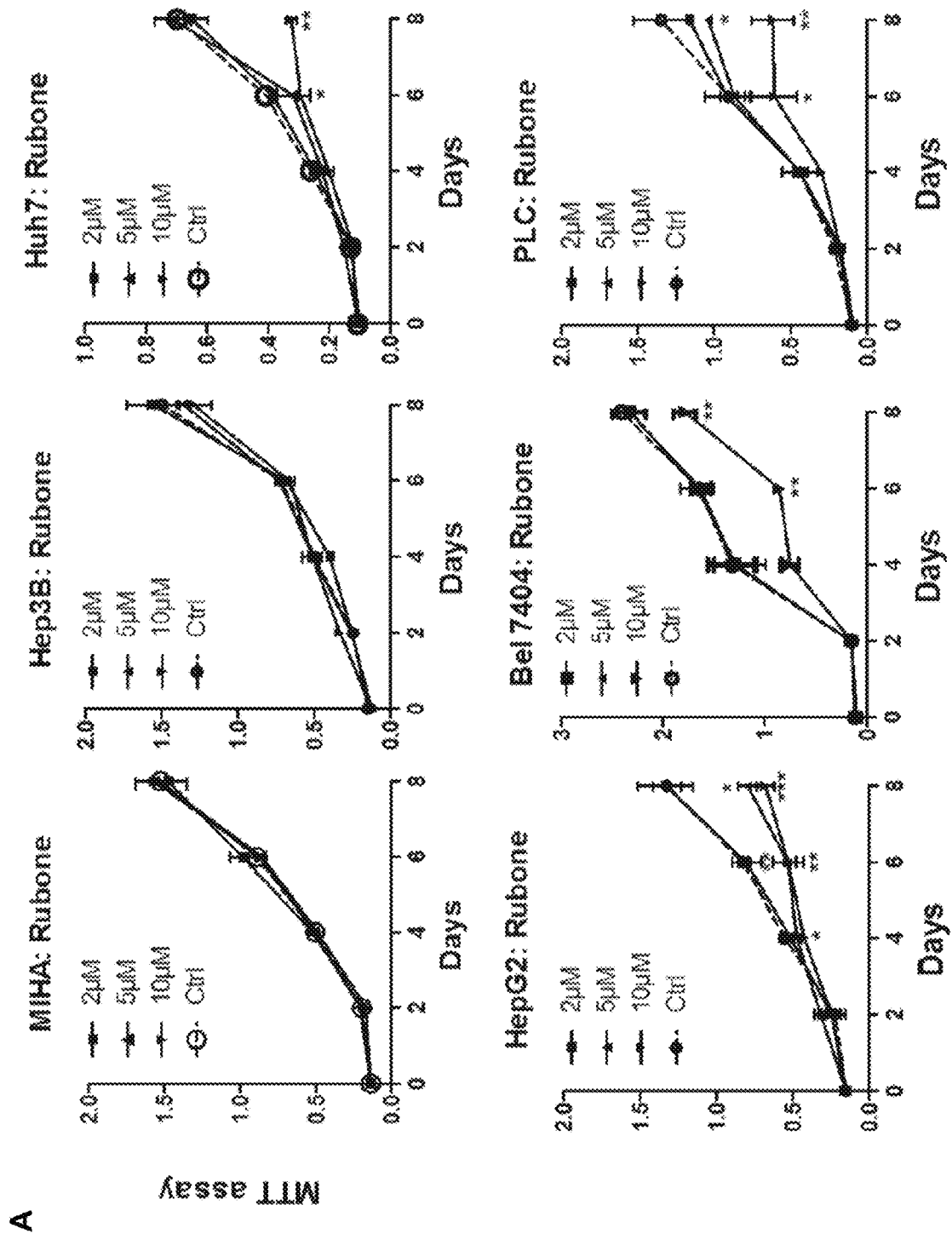
FIG. 6: Rubone inhibited HCC cell growth in vitro. (A) HCC cell lines: HepG2, Huh7, Hep3B, Bel-7404, PLC/PRF/5 and non-tumorigenic human hepatocyte cell line MIHA were treated with compound Rubone at indicated concentrations and time points. MTT assay was used to measure cell viability. Absorbance was measured at 570 nm. Absorbance values means and 95% confidence intervals of an experiment representative of three independent experiments were performed. (B) Rubone inhibited HCC cell growth by modulating miR-34a expression. Bel-7404 and PLC cells were treated with Rubone at the concentration of 10 μM alone or in combination with 2 μM miR-34a mimics or inhibitors for 72 h. MTT assays were performed to measure cell viability. The means and error bars represent 95% confidence intervals from three independent experiments.
Figure 6:
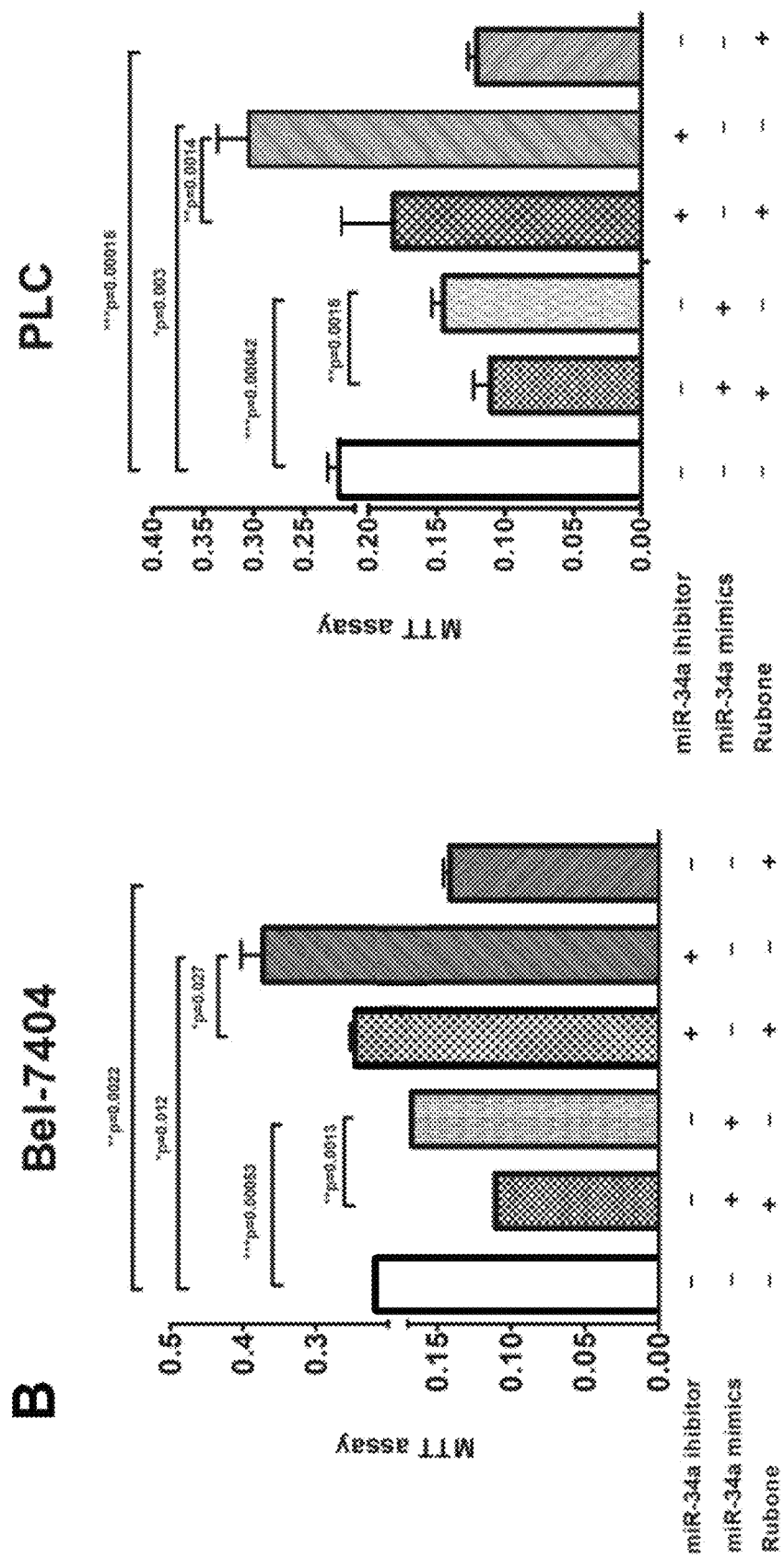

We next examined the anti-cancer activity of Rubone in vitro. Five HCC cell lines and MIHA cell line were treated with different concentrations of Rubone at indicated time points. Cell viability was measured by MTT assay. Rubone inhibited the growth of HCC cells slightly at a low concentration of 5 μM. A higher concentration of 10 μM of this compound significantly inhibited the growth of HepG2, Huh7, Bel-7404, and PLC cells. However, there were little changes in the growth rate of MIHA and Hep3B cells after treatment with Rubone (FIG. 6A).

We next asked whether Rubone inhibited HCC cell growth through miR-34a. Bel-7404 and PLC cells were transfected with miR-34a mimics or inhibitors and then treated with Rubone. FIG. 6B showed that miR-34a mimics enhanced the chemosensitivity of both HCC cell lines to Rubone. However, miR-34a inhibitors reversed the growth inhibitory effect of Rubone. These results indicated that Rubone inhibited HCC growth by modulating miR-34a expression.

MiR-34a Modulator Inhibited Hepatocellular Tumor Growth In Vivo

Figure 7:
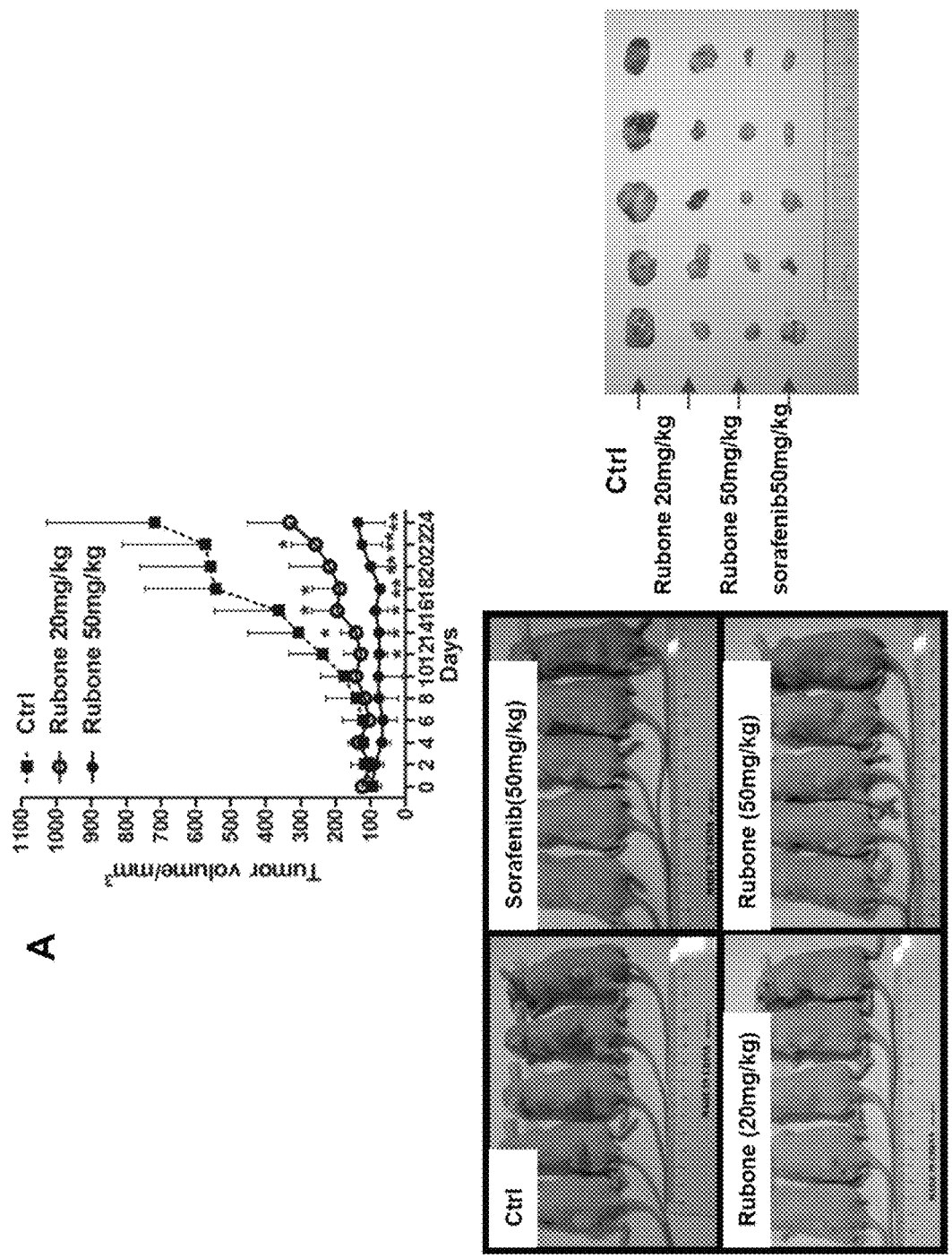
FIG. 7: Rubone inhibited HepG2 xenografted tumor growth in nude mice. (A) Rubone inhibited hepatocellular tumor growth in vivo at a dose-dependent manner. HepG2 cells were subcutaneously injected into the left flank of nude mice to establish xenograft tumor mice model. The tumor bearing nude mice were oral gavaged with Rubone at the dosages of 20 mg/kg and 50 mg/kg or sorafenib at the dose of 50 mg/kg once every two days. Tumor volume and body weight of the mice were measured. 24 days after the gavage, mice were sacrificed by carbon dioxide narcosis. Tumors were excised, sectioned and weighted. Error bars=95% confidence intervals. Photographs of representative tumors excised from nude mice at Day 24. Scale bars=1 cm. (B) Comparing the hepatocellular tumor inhibition of Rubone and Sorafenib in vivo. (C) Modulation of miR-34a and its targets by Rubone in vivo. RNA was extracted from the excised tumors. MiR-34a, cyclin D1 and Bcl-2 levels were measured by qRT-PCR. The means and error bars represent 95% confidence intervals from three independent experiments.
Figure 7:
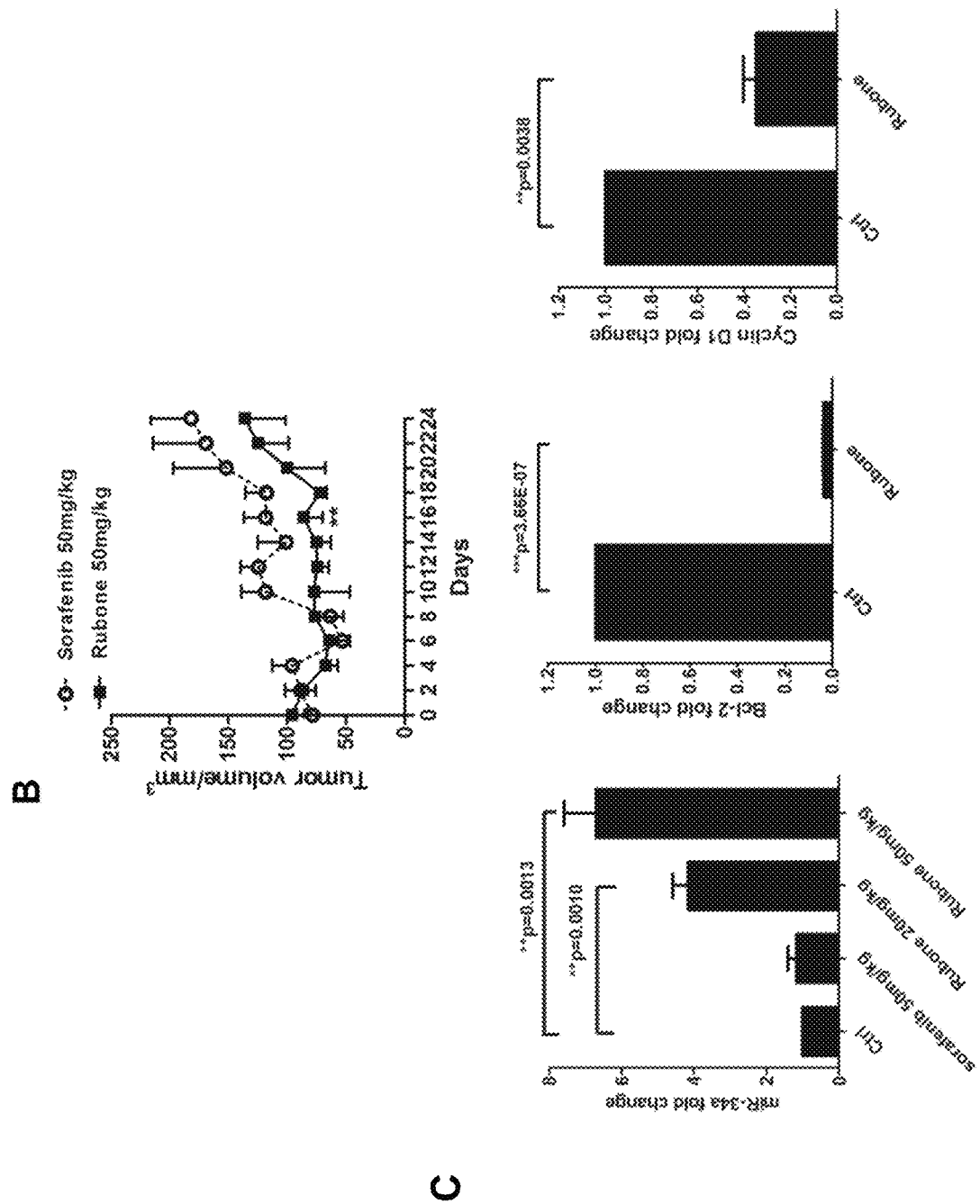

We next examined the in vivo anti-cancer activities of Rubone in HepG2 xenografted nude mice model. The tumor bearing mice were gavaged with Rubone. The anti-HCC agent Sorafenib was used as positive control. As shown in FIG. 7A and table 2, the tumors in vehicle control showed a fast and stable growth. HepG2 xenografts were sensitive to Sorafenib with a tumor growth inhibition rate at 84.22% (p=0.0013 vs. vehicle control) at the dose of 50 mg/kg. Rubone delayed the growth of tumors by 78.27% (p=0.0070 vs. vehicle control) and 89.64% (p=0.0010 vs. vehicle control) at the dose of 20 mg/kg and 50 mg/kg respectively. Rubone exhibited a stronger tumor growth inhibition than Sorafenib at the same dosage of 50 mg/kg (p=0.047 vs. sorafenib treated group) (table 2). When compared the anti-cancer activities of Rubone and Sorafenib during the whole treatment process, the results also revealed that Rubone exhibited a higher anti-cancer activities than that of Sorafenib (FIG. 7B).

MiR-34a Modulator Inhibited Angiogenesis

We found that the subcutaneous tumors treated with Rubone were visibly less vascularized compared with the control group. Tumors were then immune stained with endothelial marker CD31. The new blood vessels were highly vascularized in the control group, while tumors treated with Rubone had significantly reduced microvessels (FIG. 10A) (Rubone treated group: tube score mean=12.50, 95% CI=0.4865-24.51, p=0.0098, control group: tube score mean=67.50, 95% CI=41.95-93.04).

Figure 10:
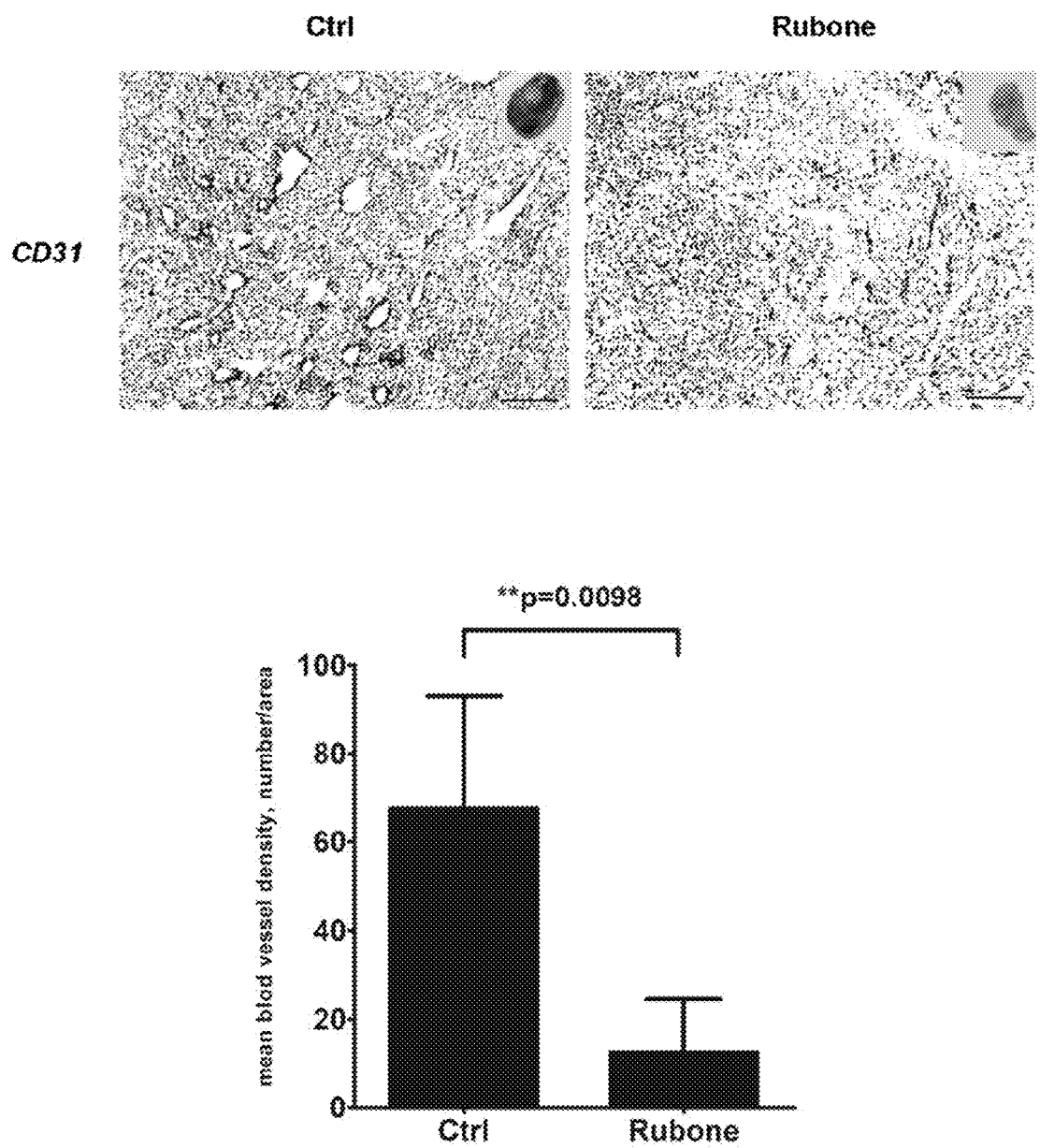
FIG. 10: Rubone inhibited angiogenesis of HepG2 xenografted tumors. (A) Rubone diminished vascularity in HepG2 xenografted tumors from nude mice. Tumor vascularity was assessed by IHC staining for CD31 antigen in tumors from Rubone treated groups. IHC staining represents endothelial cells (brown) and tumor cell nuclei (blue) in photo image. The graph (right panel) shows the mean microvessel density from each treatment group (Scale bars=50 μm). Mean microvessel density was calculated by averaging vessel counts from three random fields per slide. Each slide represents tumor from one mouse. At least three slides per treatment group were examined. Error bars represent 95% confidence intervals. Comparison between groups was performed by Student's t test. (B) Rubone inhibited endothelial cell tube formation. $2 \times 10^4$ human umbilical vein endothelial cells (HUVECs) were plated in 48-well plates coated with Matrigel and maintained in full endothelial cell growth medium. Rubone or vehicle was added to HUVECs before plating. Tube formation was assessed after 16 h of incubation (Scale bars=10 μm). Tube formation was quantitated. The total tubes were measured with the aid of imaging analysis software from the microphotographs. Each well was taken at ×40 magnifications. Results were presented tube numbers relative to control (vehicle DMSO treated HUVECs). Error bars represent 95% confidence intervals from three independent experiments. Comparison between groups was performed by Student's t test.
Figure 10:
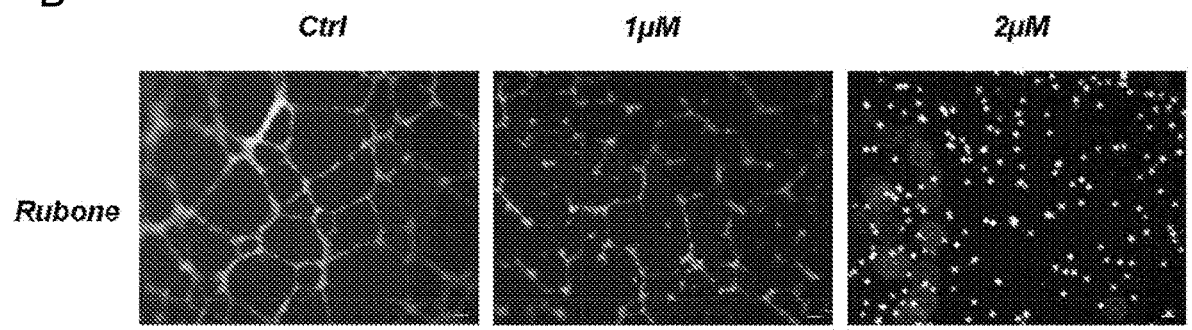
Figure 10:
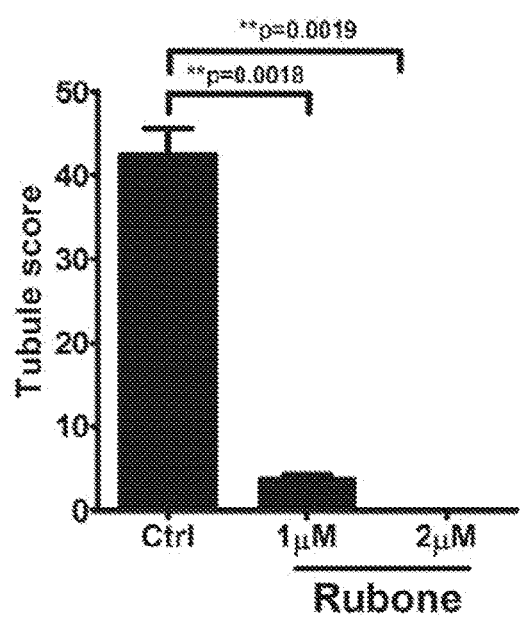

We next examined whether Rubone could inhibit tube formation of HUVECs in vitro. HUVECs treated with vehicle control underwent rapid reorganization (visible within 1-2 h) and subsequently formed capillary-like structures. In contrast, treatment with Rubone caused a dose-dependent inhibition of ECM gel-induced network formation at 4 h. There was significant inhibition at lower concentration of 1 μM of Rubone compared to the control group (Rubone treated group: tube score, 3.667, 95% CI=2.232-5.101, p=0.0036; control group: mean of tube score, 42.33, 95% CI=34.35-50.32). Meanwhile, after treatment of Rubone, the tube lengths were shorter; the tubes were less extensive, thinner and foreshortened. Treatment with a higher dose at 2 μM of Rubone, no tubes formed at all (FIG. 10B). These findings confirmed that miR-34a modulator could modify endothelial cell functions and suggested that Rubone might indeed prevent the process of angiogenesis to repress tumor growth.

MiR-34a Modulator Increased miR-34a Promoter Activities and p53 Occupancy on miR-34a Promoter Since both primary and mature miR-34a were dramatically increased after treatment with Rubone, we next examined whether Rubone could modulate miR-34a promoter activity. HCC cell lines with different p53 status (HepG2: p53 wild type, Bel-7404: p53 mutant, Hep3B: p53 deletion)

TABLE 2

| | | HepG2 xenograft model | | |
|---|---|---|---|---|
| Drugs and dosage | Mice survival (n) initial/end | Body weight (g)a initial/end | Tumor weight (g)b | Tumor growth inhibition (%) |
| Vehicle | 5/5 | 18.80(95% CI = 16.96 – 20.64)/ 23.00(95% CI = 21.04 – 24.96) | 1.178 (95% CI = 0.82 – 1.54) | — |
| Rubone (20 mg/kg) | 5/5 | 19.60(95% CI = 18.49 – 20.71)/ 23.60(95% CI = 21.93 – 25.27) | 0.256 (95% CI = 0.08 – 0.42)** | 78.27 |
| Rubone (50 mg/kg) | 5/5 | 20.00(95% CI = 20.00 – 20.00)/ 23.60(95% CI = 21.03 – 26.17) | 0.122 (95% CI = 0.067 – 0.18)** # | 89.64 |
| Sorafenib (50 mg/kg) | 5/5 | 20.00(95% CI = 18.76 – 21.24)/ 24.00(95% CI = 21.22 – 26.78) | 0.186 (95% CI = 0.14 – 0.23)** | 84.22 |

Figure 8:
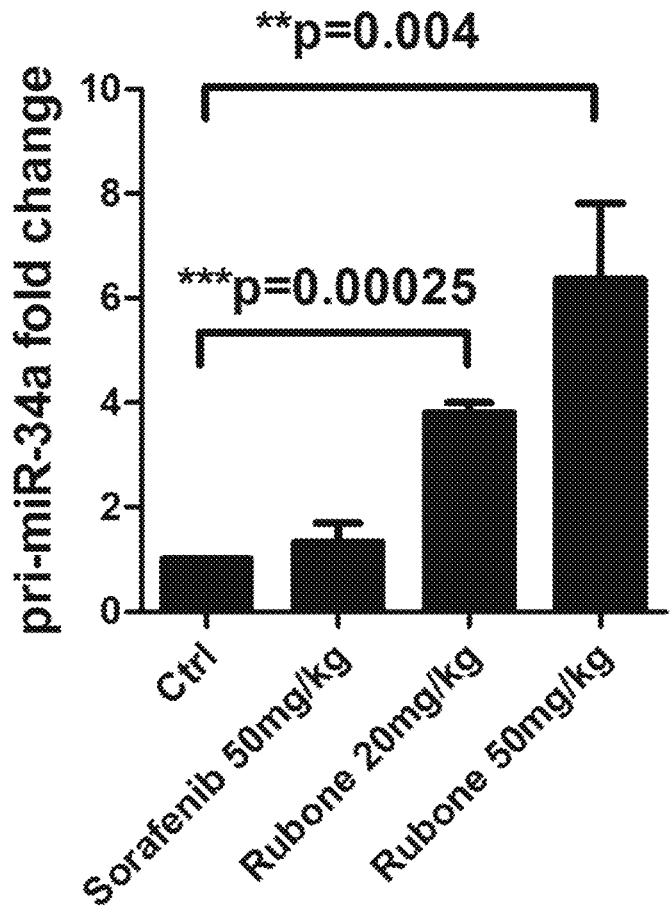
FIG. 8: Rubone activated pri-miR-34a expressions in HepG2 xenograft tumors. Tumor bearing nude mice were gavaged with Rubone, Sorafenib or vehicle once every two days. The tumors were excised after sacrificing the mice. RNA was extracted from the tumors. qRT-PCR were applied to measure pri-miR-34a levels in these tumors. Error bars=95% confidence intervals from three independent experiments.
Figure 11:
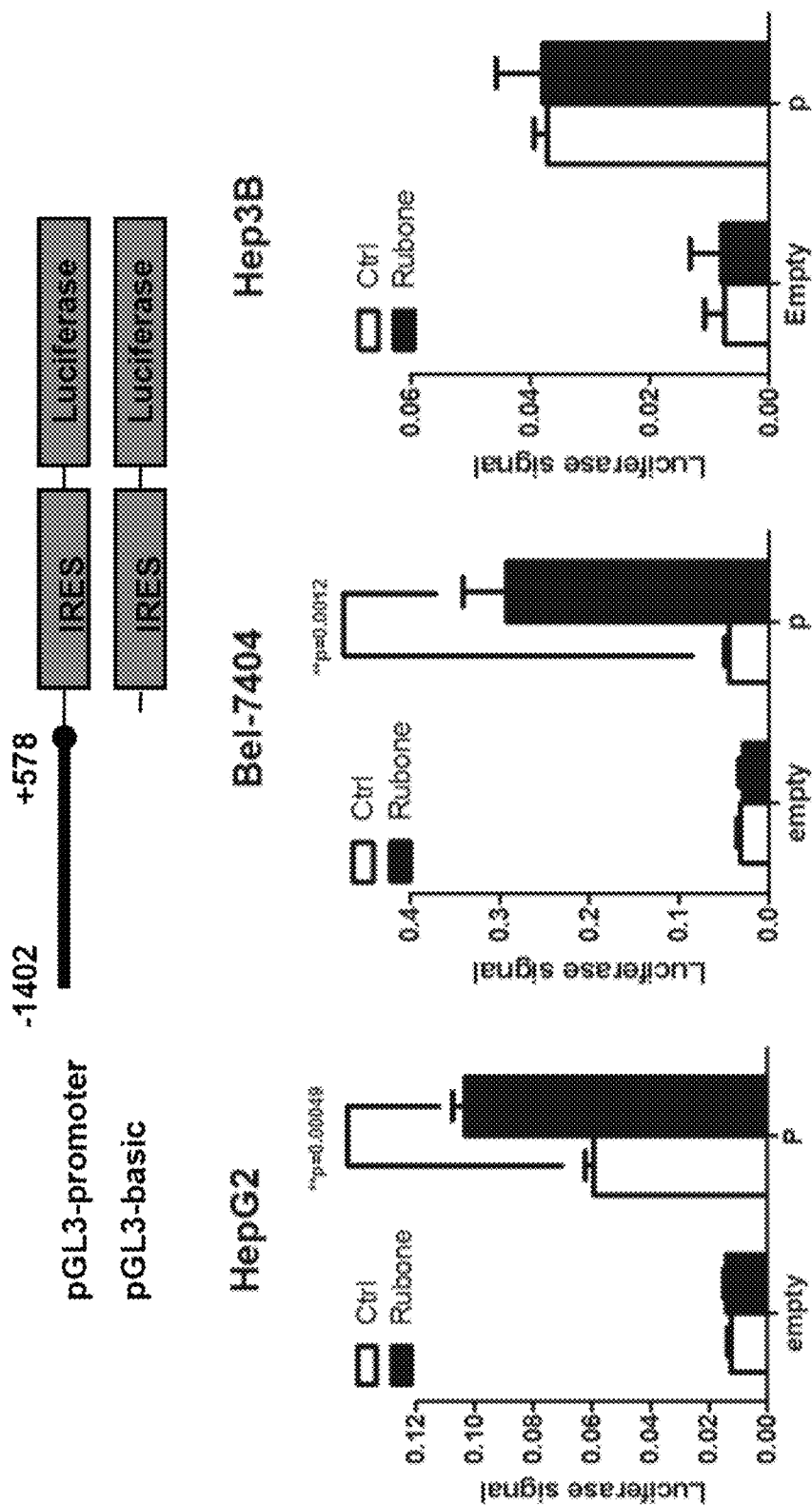
FIG. 11: Rubone activates miR-34a expression by increasing p53 activities. (A) Rubone modulated miR-34a promoter activity. The full length miR-34a promoter including p53 binding site in pGL-3 plasmid was transfected into HepG2, Hep3B and Bel-7404 cells. The luciferase activities were measured afte 10 μM Rubone treatment. (B, C) Knockdown of p53 reversed miR-34a expression and cell growth inhibition induced by Rubone in HepG2 and Bel-7404 cells. HepG2 and Bel-7404 cells were transfected with 2 μM siRNAs targeting p53, and then treated with 10 μM Rubone. MiR-34a level was measured by qRT-PCR. Cell viability was measured by MTT assay. (D) Rubone increased p53 occupancy on miR-34a promoter. ChIP assay was applied in HepG2 and Bel-7404 cells treated with 10 μM Rubone. qPCR was employed to quality the p53 occupancy on miR-34a promoter region. Error bars represent 95% confidence intervals from three independent experiments. Comparison between groups was performed by Student's t test.
Figure 11:
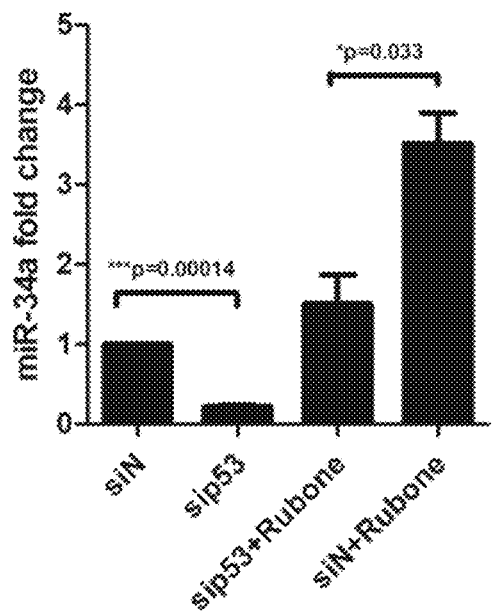
Figure 11:
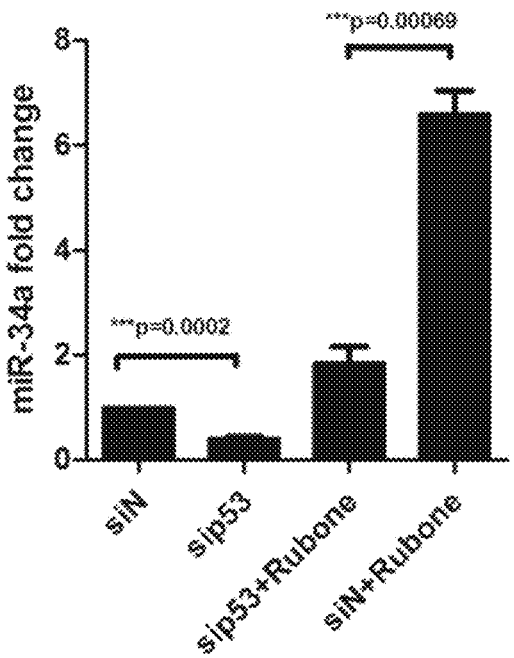
Figure 11:
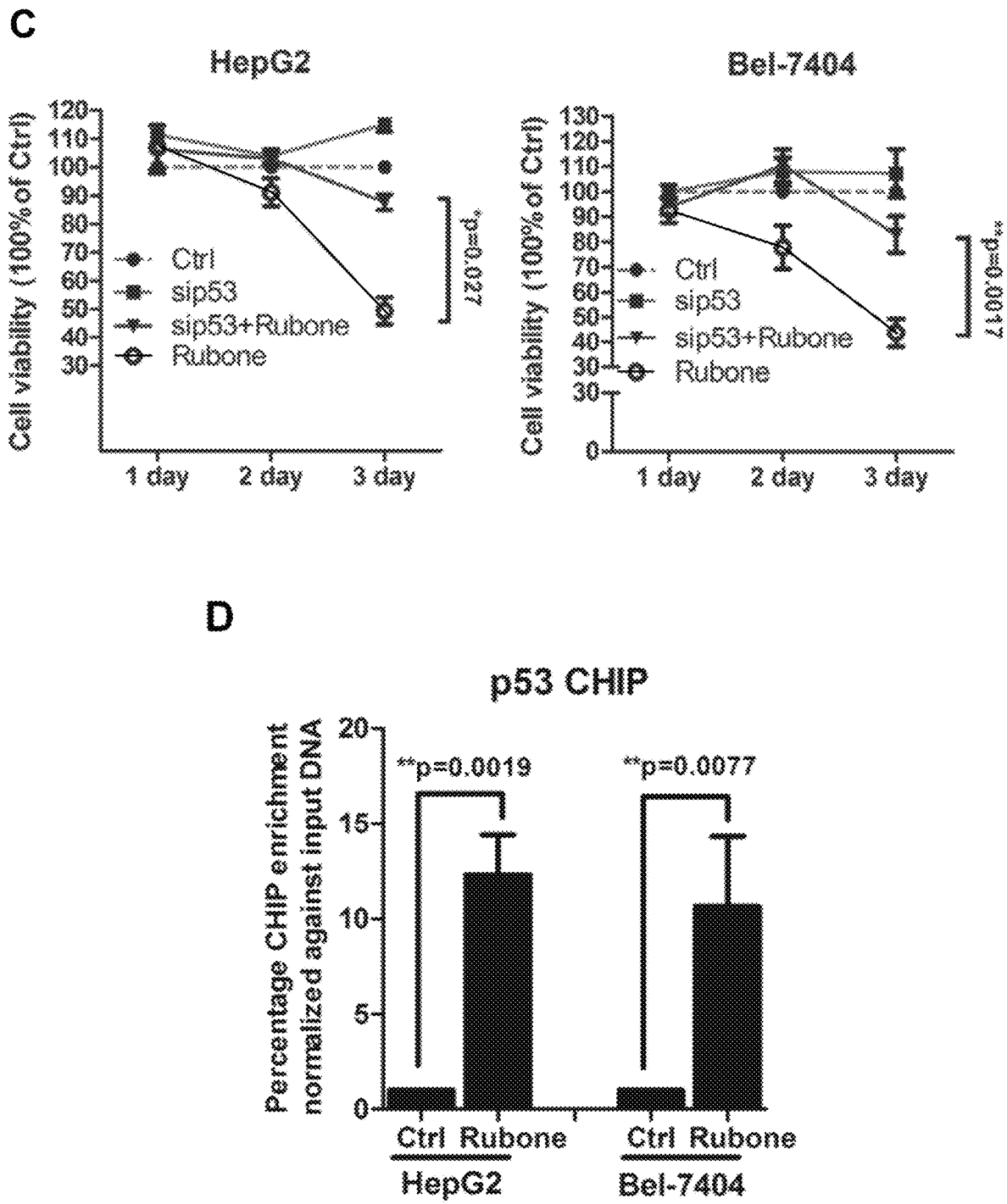

The expression levels of pri-miR-34a, miR-34a, Cyclin D1 and Bcl-2 in the xenografted tumors were measured by qRT-PCR. In Rubone treated tumors, both pri-miR-34a and miR-34a levels were up-regulated, while miR-34a targets Cyclin D1 and Bcl-2 were down-regulated (FIG. 7C and FIG. 8). Sorafenib treatment caused no changes in the expression of miR-34a and its targets (FIG. 7C). Moreover, there was no obvious body weight loss in the treated mice compared with vehicle control (table 2). No obvious side effect was observed at the end of experiment. These results indicated that Rubone was an effective and safe anti-HCC agent in animal.

were used for promoter activity assay. These three cell lines were first transfected with miR-34a promoter and then treated with Rubone. MiR-34a promoter activities were both increased in both HepG2 and Bel-7404 cells after Rubone treatment. However, there was no change in miR-34a promoter activity after Rubone treatments in Hep3B cells (FIG. 11A). These results suggested a potential role of p53 in Rubone modulation on miR-34a promoter activity.

Figure 9:
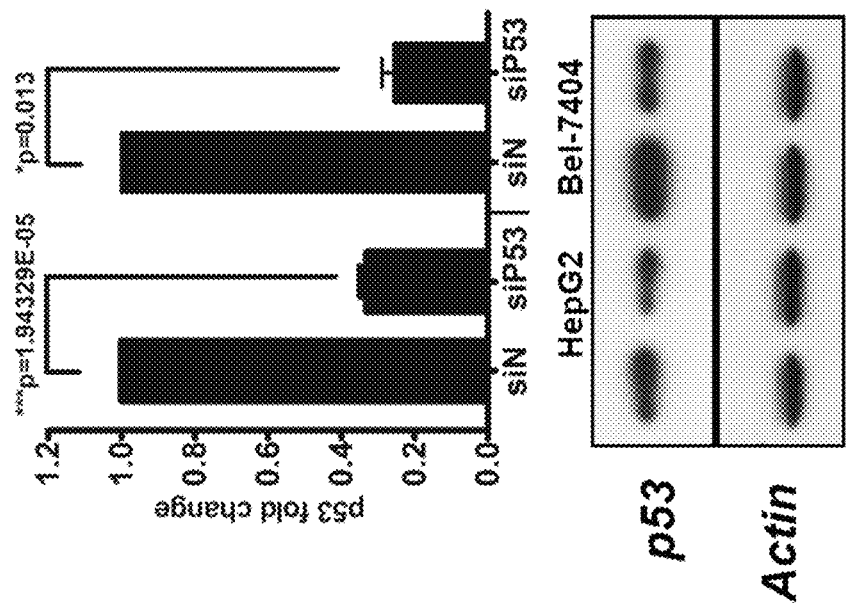
FIG. 9: Rubone activated pri-miR-34a expressions without changing p53 expression. (A) Quantification of p53 expression levels by RT-PCR in HepG2, Huh7 and Bel-7404 cells after 10 μM Rubone treatment. (B) P53 mRNA and protein levels were decreased in HepG2 and Bel-7404 cells by sip53. (C) Increased pri-miR-34a levels in HCC cells induced by Rubone were reversed by p53 knockdown. All the means and 95% confidence intervals (error bars) are presented from three independent experiments.
Figure 9:
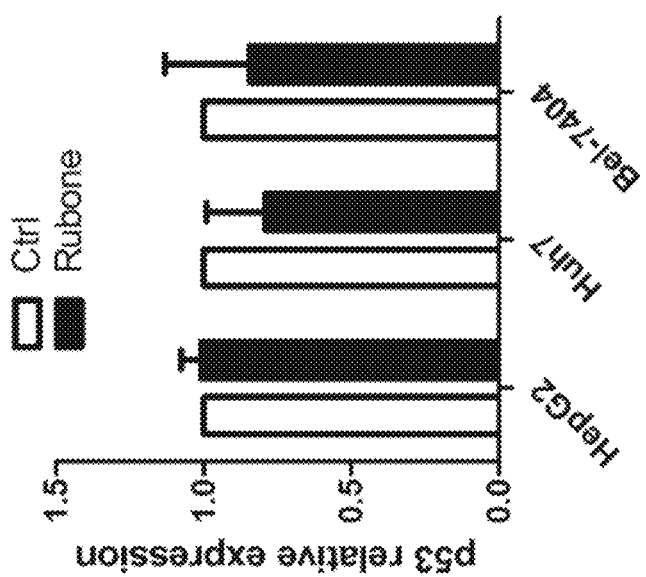
Figure 9:
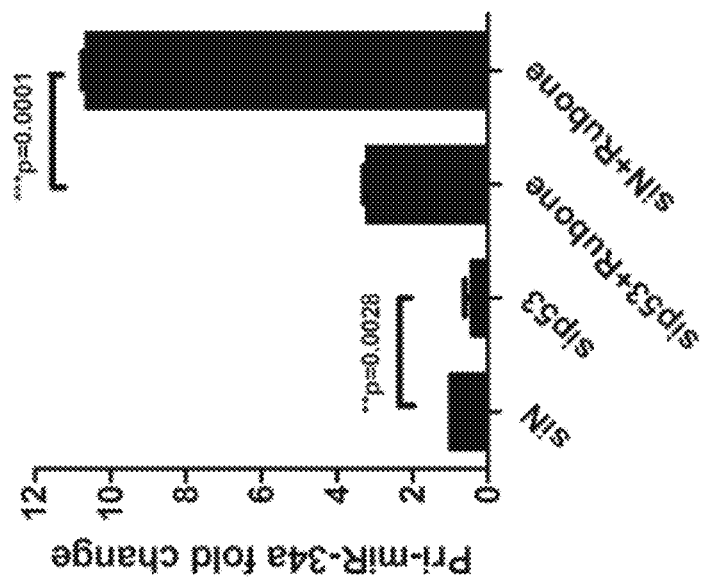
Figure 9:
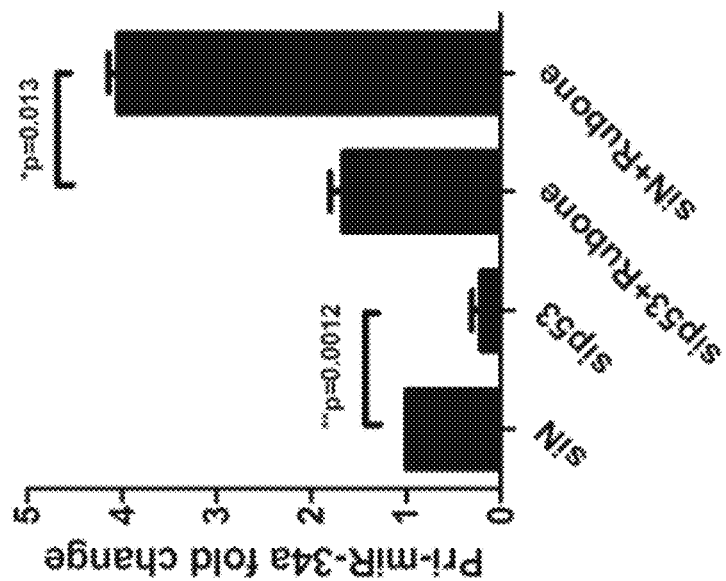

We employed siRNAs to knock down p53 in HepG2 and Bel-7404 cells (FIG. 9B). HepG2 and Bel-7404 cells were then treated with Rubone. The siRNAs used targeted both wild type and mutant p53. qRT-PCR results showed that miR-34a levels decreased after p53 knockdown (FIG. 11B).

Moreover, the increased expression levels of miR-34a by Rubone were significantly reversed by p53 knockdown (FIG. 11B). Meanwhile, pri-miR-34a expressions exhibited similar changes with that of miR-34a in HepG2 and Bel-7404 cells (FIG. 9C). MTT assay further revealed that the growth inhibitory effects of Rubone on HCC cells were also significantly reversed by knocking down p53 (FIG. 11C). These results suggested that p53 plays important roles in the biological activity of Rubone. We next employed ChIP assay to examine whether Rubone could modulate p53 activities. The results showed that Rubone treatment significantly increased p53 occupancy on miR-34a promoter in both HepG2 and Bel-7404 cells (FIG. 11D).

Discussion

In this study, one hit compound named Rubone was found to restore miR-34a expression in HCC cell with miR-34a silencing. Rubone is a chemically synthesized plant chalcone derivative. Rubone has not been previously reported to have any known biological activities. This compound offered us a new option for cancer treatment.

Our studies showed that Rubone could dramatically increase miR-34a expression while decrease miR-34a targets expression (FIGS. 3 and 5). Moreover, Rubone caused no change in the expression of other microRNAs in HCC cells. Especially, this compound did not change other p53 regulated miRNAs expression, such as miR-34c, miR-145, miR-192, miR-215 (27). Furthermore, other common used anti-HCC agents treatments including CDDP, 5-FU, Dox and Sorafenib have no effect on miR-34a expression (FIG. 4B). These results indicated that Rubone specifically modulated miR-34a expression. We found that Rubone could inhibit HCC cell growth at dose- and time-dependent manners. We further found that Rubone exhibited their anti-cancer activity through miR-34a because miR-34a mimics enhanced the chemosensitivity of HCC cells to this compound. However, miR-34a inhibitors reversed the growth inhibitory effect of Rubone on HCC cells. Our results suggested that miR-34a was the drug target of Rubone.

We further demonstrated that Rubone exhibited strong anti-cancer efficacy in HepG2 xenografted mouse model. We also found that both pri-miR-34a and miR-34a expression levels were up-regulated in HCC tumors in vivo after treatment with Rubone. The miR-34a targets Cyclin D1 and Bcl-2 were down-regulated in HepG2 xenografted tumors. All these results were consistent with the in vitro studies. The in vivo testing further confirmed the strong anti-cancer activity of Rubone.

Currently, the efficacy of chemotherapeutic drugs for HCC is limited (28). Sorafenib is a forefront of therapy for HCC. Sorafenib showed certain efficacy for HCC patients by inhibiting Raf-1 and vascular endothelial growth factor (VEGF) pathways (29). However, Sorafenib showed serious side effects such as hand-foot skin reaction (30), eruptive melanocytic lesions (31) and so on. Therefore, it is still of urgent clinical significance to develop novel therapeutic with better efficacy and less side effects.

Our results showed that the anti-cancer efficacy of Rubone is higher than Sorafenib. Therefore, Rubone warrants further investigation as a potential effective anti-HCC agent. Meanwhile, both in vitro and in vivo studies demonstrated that Rubone could modify endothelial cell functions. Previous study showed that miR-34a overexpression led to significantly increased endothelial progenitor cell (EPC) senescence and diminished EPC angiogenesis (32). Our studies suggested that Rubone might indeed prevent the process of angiogenesis to repress tumor growth.

Previous study has revealed p53 could directly and positively regulate the expression of miR-34a (9). More than 50% of human tumors contain mutation or deletion of p53 gene (33). However, there are still no report on the relationships between miR-34a and mutant p53. Rubone modulated miR-34a expression in HCC cells with both wild type and mutant p53 but not in HCC cells with p53 deletion. Our results showed that the upregulation of miR-34a by Rubone was significantly reversed after p53 knockdown. And the growth inhibitory effects of Rubone on these cell lines were also reversed by p53 knockdown. The results suggested for the first time that mutant p53 could also modulate miR-34a expression. Rubone increased miR-34a promoter activities, suggesting that Rubone modulated miR-34a expression at transcriptional level. However, we found p53 expression was not affected by Rubone treatments (FIG. 9A). We hypothesized whether Rubone modulated miR-34a expression by increasing p53 activity. Finally, ChIP assay results indicated that Rubone treatment significantly increased the occupancy of p53 on miR-34a promoter. In summary, our study firstly identified a small miR-34a modulator with strong anti-cancer activity against HCC. Rubone modulated miR-34a expression by increasing p53 activity. The anti-cancer mechanism is quite different from the commonly used anti-cancer agents.

REFERENCES

1. Pisani P, Parkin D M, Bray F I, Ferlay J. Estimates of the worldwide mortality from twenty five major cancers in 1990. Int J Cancer 1999; 83:18-29.
2. Carthew R W. Gene regulation by microRNAs. Curr Opin Genet Dev 2006; 16:203-8.
3. Lewis B P, Burge C B, Bartel D P. Conserved seed pairing, often flanked by adenosines, indicates that thousands of human genes are microRNA targets. Cell 2005; 120:15-20.
4. Friedman R C, Farh K K, Burge C B, Bartel D P. Most mammalian mRNAs are conserved targets of microRNAs. Genome Res 2009; 19:92-105.
5. Selbach M, Schwanhausser B, Thierfelder N, Fang Z, Khanin R, Rajewsky N. Widespread changes in protein synthesis induced by microRNAs. Nature 2008; 455: 58-63.
6. Ha T Y. MicroRNAs in Human Diseases: From Cancer to Cardiovascular Disease. Immune Netw 2011; 11:135-54.
7. Hwang H W, Mendell J T. MicroRNAs in cell proliferation, cell death, and tumorigenesis. Br J Cancer 2006; 94:776-80.
8. Janssen H L, Reesink H W, Lawitz E J, Zeuzem S, Rodriguez-Tones M, Patel K, et al. Treatment of HCV infection by targeting microRNA. N Engl J Med 2013; 368:1685-94.
9. He L, He X, Lim L P, Stanchina E D, Xuan Z, Liang Y, et al. MicroRNA component of the p53 tumor suppressor network. Nature 2003; 447:1130-4.
10. Welch C, Chen Y, R. L. Stallings. MicroRNA-34a functions as a potential tumor suppressor by inducing apoptosis in neuroblastoma cells. Oncogene 2007; 26: 5017-22.
11. Sun F, Fu H, Liu Q, Tie Y, Zhu J, Xing R, et al. Downregulation of CCND1 and CDK6 by miR-34a induces cell cycle arrest. FEBS Lett 2008; 582:1564-8.
12. Ji X M, Wang Z W, Geamanu A, Goja A, Sarkar F H, Gupta S V. Delta-tocotrienol suppresses Notch-1 pathway by upregulating miR-34a in nonsmall cell lung cancer cells. Int J Cancer 2012; 131:2668-77.

13. Toyota M, Suzuki H, Sasaki Y, Maruyama R, Imai K, Shinomura Y, et al. Epigenetic silencing of microRNA-34b/c and B-cell translocation gene 4 is associated with CpG island methylation in colorectal cancer. Cancer Res 2008; 68:4123-32.
14. Hashimi S T, Fulcher J A, Chang M H, Gov L, Wang S, Lee B. MicroRNA profiling identifies miR-34a and miR-21 and their target genes JAG1 and WNT1 in the coordinate regulation of dendritic cell differentiation. Blood 2009; 114: 404-14.
15. Li Y, Guessous F, Zhang Y, Dipierro C, Kefas B, Johnson E, et al. microRNA-34a inhibits glioblastoma growth by targeting multiple oncogenes. Cancer Res 2009; 69:7569-76.
16. Yamakuchi M, Ferlito M, Lowenstein C J. MiR-34a repression of SIRT1 regulates apoptosis. Proc Natl Acad Sci USA 2008; 105:13421-6.
17. Li N, Fu H, Tie Y. MiR-34a inhibits migration and invasion by down-regulation of c-Met expression in human hepatocellular carcinoma cells. Cancer Lett 2009; 275:44-53.
18. Gumireddy K, Young D D, Xiong X, Hogenesch J B, Huang Q, Deiters A. Small-molecule inhibitors of microrna miR-21 function. Angew Chem Int Ed Engl 2008; 47:7482-4.
19. Young D D, Connelly C M, Grohmann C, Deiters A. Small molecule modifiers of microRNA miR-122 function for the treatment of hepatitis C virus infection and hepatocellular carcinoma. J Am Chem Soc 2010; 132: 7976-81.
20. Bommer G T, Gerin I, Feng Y, Kaczorowski A J, Kuick R, Love R E. P53-mediated activation of miRNA-34 candidate tumor-suppressor genes. Curr Biol 2007; 17:1298-307.
21. Chang T C, Wentzel E A, Kent O A, Ramachandran K, Mullendore M, Lee K H, et al. Transactivation of miR-34a by p53 broadly influences gene expression and promotes apoptosis. Mol Cell 2007; 26:745-52.
22. Tarasov V, Jung P, Verdoodt B, Lodygin D, Epanchintsev A, Menssen A, et al. Differential regulation of microRNAs by p53 revealed by massively parallel sequencing: miR-34a is a p53 target that induces apoptosis and G1-arrest. Cell Cycle 2007; 6:1586-93.
23. Tazawa H, Tsuchiya N, Izumiya M, Nakagama H. Tumor-suppressive miR-34a induces senescence-like growth arrest through modulation of the E2F pathway in human colon cancer cells. Proc Natl Acad Sci USA 2007; 104:15472-7.
24. Raver-Shapira N, Marciano E, Meiri E, Spector Y, Rosenfeld N, Moskovits N, et al. Transcriptional activation of miR-34a contributes to p53-mediated apoptosis. Mol Cell 2007; 26:731-43.
25. Chen Y, Lin M C, Yao H, Wang H, Zhang A Q, Yu J, et al. Lentivirus-mediated RNA interference targeting enhancer of zeste homolog 2 inhibits hepatocellular carcinoma growth through down-regulation of stathmin. Hepatology 2007; 46:200-8.
26. Li C H, To K F, Tong J H, Xiao Z, Xia T, Lai P B, et al. Enhancer of zeste homolog 2 silences miR-218 in human pancreatic ductal adenocarcinoma cells by inducing formation of heterochromatin. Gastroenterology 2013; 144: 1086-97.
27. Feng Z, Zhang C, Wu R, Hu W. Tumor suppressor p53 meets microRNAs. J Mol Cell Biol 2011; 3:44-50.
28. Lee J, Park J O, Kim W S, Park S H, Park K W, Choi M S, et al. Phase II study of doxorubicin and cisplatin in patients with metastatic hepatocellular carcinoma. Cancer Chemother Pharmacol 2004; 54:385-90.
29. Llovet J M, Ricci S, Mazzaferro V, Hilgard P, Gane E, Blanc J F, et al. Sorafenib in advanced hepatocellular carcinoma. N Engl J Med 2008; 359:378-90.
30. Lacouture M E, Reilly L M, Gerami P, Guitart J. Hand foot skin reaction in cancer patients treated with the multikinase inhibitors sorafenib and sunitinib. Ann Oncol 2008; 19:1955-61.
31. Kong H H, Sibaud V, Chanco Turner M L. Sorafenib-induced eruptive melanocytic lesions Arch Dermatol 2008; 144:820-2.
32. Zhao t, Li J, Chen A F. MicroRNA-34a induces endothelial progenitor cell senescence and impedes its angiogenesis via suppressing silent information regulator 1. Am J Physiol Endocrinol Metab 2010; 299:110-6.
33. Levine A J. p53: the cellular gatekeeper for growth and division. Cell 1997; 88:323-31.

What is claimed is:

1. A method of inhibiting human cancer cell proliferation comprising contacting a human cancer cell with an effective amount of:

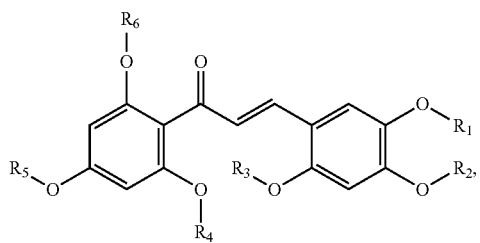

wherein $R_1$-$R_5$ is $CH_3$, and $R_6$ is H, and
wherein the effective amount is an amount effective to increase miRNA-34a expression in the human cancer cell and wherein p53 gene in the human cancer cell is wild-type or mutated but not deleted.

2. The method of claim 1, wherein the human cancer cell is present in a human patient.

3. The method of claim 2, wherein the contacting step comprises subcutaneous, intramuscular, intravenous, intraperitoneal, or oral administration.

4. The method of claim 3, wherein the method further comprises administering an anti-anemia compound, an anti-nausea compound, an anti-inflammatory, an immunomodulator, or a chemotherapeutic.

5. The method of claim 1, wherein the miRNA-34a expression is increased at least 3-fold in comparison to miRNA-34a expression level in a mammalian cell that has not been contacted.

6. The method of claim 1, wherein the method further comprises detecting activation of miRNA-34a expression with a polynucleotide encoding a reporter gene.

7. The method of claim 6, wherein the polynucleotide encoding a reporter gene comprises a sequence encoding for a luciferase or a fluorescent protein.

8. The method of claim 1, wherein the human cancer cell is a human breast cancer cell.

9. The method of claim 3, wherein the human cancer cell is a human colorectal cancer cell.

10. The method of claim 1, wherein the human cancer cell is a human liver cancer cell.

11. The method of claim 1, wherein the human cancer cell is a human lung cancer cell.

12. The method of claim 1, wherein the human cancer cell is a human prostate cancer cell.

* * * * *